(12) United States Patent
Arlotti et al.

(10) Patent No.: US 12,311,180 B2
(45) Date of Patent: May 27, 2025

(54) SYSTEMS AND METHODS FOR ADAPTIVE DEEP BRAIN STIMULATION

(71) Applicant: Newronika S.p.A., Milan (IT)

(72) Inventors: Mattia Arlotti, Monza Brianza (IT); Lorenzo Rossi, Trento (IT)

(73) Assignee: Newronika S.p.A., Milan (IT)

(*) Notice: Subject to any disclaimer, the term of this patent is extended or adjusted under 35 U.S.C. 154(b) by 805 days.

(21) Appl. No.: 17/378,033

(22) Filed: Jul. 16, 2021

(65) Prior Publication Data

US 2022/0016415 A1 Jan. 20, 2022

Related U.S. Application Data

(60) Provisional application No. 63/053,263, filed on Jul. 17, 2020.

(51) Int. Cl.
*G16H 10/60* (2018.01)
*A61N 1/36* (2006.01)
(Continued)

(52) U.S. Cl.
CPC ..... *A61N 1/36175* (2013.01); *A61N 1/36171* (2013.01); *A61N 1/36192* (2013.01);
(Continued)

(58) Field of Classification Search
CPC .................................................... G16H 10/60
See application file for complete search history.

(56) References Cited

U.S. PATENT DOCUMENTS 5,683,422 A 11/1997 Rise
6,360,122 B1 3/2002 Fischell et al.
(Continued)

FOREIGN PATENT DOCUMENTS

CN 101589549 A 11/2009
EP 2 004 036 B1 7/2011
(Continued)

OTHER PUBLICATIONS

Sakkalis V, et al., Parametric and nonparametric EEG analysis for the evaluation of EEG activity in young children with controlled epilepsy, 2008; Comput Intell Neurosci., 2008:462593. doi: 10.1155/2008/462593. (Year: 2008).*
(Continued)

*Primary Examiner* — Evangeline Barr
(74) *Attorney, Agent, or Firm* — COOLEY LLP

(57) ABSTRACT

In some variations provided herein, a system for deep brain stimulation includes an implantable device that acquire and store neural activity signal records and apply electrical stimulation. The system further includes a personal controller device that establishes a first wireless connection to the implantable device. The personal controller device transmits power to the implantable device, and the implantable device transmits neural activity signal records to the personal controller device over the first wireless connection. The system further includes a clinician programmer device that receive the neural activity signal records from the implantable device by establishing a second wireless connection based on activation of the first wireless connection. The clinician programmer device sets one or more stimulation parameters based on the neural activity signal records.

14 Claims, 18 Drawing Sheets

(51) Int. Cl.
  *A61N 1/372* (2006.01)
  *A61N 1/05* (2006.01)
(52) U.S. Cl.
  CPC ......... *A61N 1/37282* (2013.01); *G16H 10/60* (2018.01); *A61N 1/0534* (2013.01); *A61N 1/3605* (2013.01)

(56) References Cited

U.S. PATENT DOCUMENTS

| | | |
|---|---|---|
| 6,366,813 B1 | 4/2002 | DiLorenzo |
| 6,473,639 B1 | 10/2002 | Fischell et al. |
| 6,480,743 B1 | 11/2002 | Kirkpatrick et al. |
| 6,820,019 B1 | 11/2004 | Kelly et al. |
| 6,873,872 B2 | 3/2005 | Gkuckman et al. |
| 6,993,384 B2 | 1/2006 | Bradley et al. |
| 7,024,247 B2 | 4/2006 | Gliner et al. |
| 7,089,059 B1 | 8/2006 | Pless |
| 7,127,296 B2 | 10/2006 | Bradley |
| 7,177,678 B1 | 2/2007 | Osorio et al. |
| 7,231,254 B2 | 6/2007 | DiLorenzo |
| 7,236,830 B2 | 6/2007 | Gliner |
| 7,277,758 B2 | 10/2007 | DiLorenzo |
| 7,385,443 B1 | 6/2008 | Denison |
| 7,620,456 B2 | 11/2009 | Gliner et al. |
| 7,787,958 B2 | 8/2010 | Stevenson |
| 7,847,628 B2 | 12/2010 | Denison |
| 8,019,419 B1 | 9/2011 | Panescu et al. |
| 8,078,281 B2 | 12/2011 | Priori et al. |
| 8,135,473 B2 | 3/2012 | Miesel et al. |
| 8,190,251 B2 | 5/2012 | Molnar et al. |
| 8,224,452 B2 | 7/2012 | Pless et al. |
| 8,280,514 B2 | 10/2012 | Lozano et al. |
| 8,396,565 B2 | 3/2013 | Singhal et al. |
| 8,423,145 B2 | 4/2013 | Pless et al. |
| 8,473,063 B2 | 6/2013 | Gupta et al. |
| 8,504,154 B2 | 8/2013 | Wanasek |
| 8,521,294 B2 | 8/2013 | Sarma et al. |
| 8,543,221 B2 | 9/2013 | Campbell et al. |
| 8,594,795 B2 | 11/2013 | Tcheng et al. |
| 8,644,930 B2 | 2/2014 | Kelly |
| 8,679,038 B1 | 3/2014 | Giuffrida |
| 8,718,757 B2 | 5/2014 | Bradley et al. |
| 8,744,587 B2 | 6/2014 | Miesel et al. |
| 8,825,175 B2 | 9/2014 | King |
| 8,892,208 B2 | 11/2014 | Flynn et al. |
| 8,942,809 B2 | 1/2015 | Assaf et al. |
| 8,954,152 B2 | 2/2015 | Gupta et al. |
| 8,983,617 B2 | 3/2015 | Chavan et al. |
| 9,002,449 B2 | 4/2015 | Kameli |
| 9,061,140 B2 | 6/2015 | Shi et al. |
| 9,089,704 B2 | 7/2015 | Kelly |
| 9,119,964 B2 | 9/2015 | Marnfeldt |
| 9,192,760 B2 | 11/2015 | Bradley et al. |
| 9,211,417 B2 | 12/2015 | Heldman et al. |
| 9,238,138 B2 | 1/2016 | Lee et al. |
| 9,248,280 B2 | 2/2016 | Moffitt et al. |
| 9,375,582 B2 | 6/2016 | Kaula et al. |
| 9,381,356 B2 | 7/2016 | Parker et al. |
| 9,399,132 B2 | 7/2016 | Parramon et al. |
| 9,421,379 B2 | 8/2016 | Zhu |
| 9,445,730 B2 | 9/2016 | Snyder et al. |
| 9,504,832 B2 | 11/2016 | Libbus et al. |
| 9,521,979 B2 | 12/2016 | Stanslaski et al. |
| 9,522,278 B1 | 12/2016 | Heldman et al. |
| 9,656,089 B2 | 5/2017 | Yip et al. |
| 9,750,938 B2 | 9/2017 | Ternes et al. |
| 9,844,676 B2 | 12/2017 | Zhang et al. |
| 9,888,861 B2 | 2/2018 | Carlson et al. |
| 10,154,812 B2 | 12/2018 | Howard |
| 10,219,697 B2 | 3/2019 | Muller |
| 10,471,259 B2 | 11/2019 | Stanslaski et al. |
| 10,596,379 B2 | 3/2020 | Arlotti et al. |
| 10,639,480 B2 | 5/2020 | Dearden et al. |
| 10,864,368 B2 | 12/2020 | Stanslaski et al. |
| 10,933,243 B2 | 3/2021 | Senderowicz et al. |
| 11,083,402 B2 | 8/2021 | Nelson et al. |
| 11,160,979 B1 | 11/2021 | Giuffrida et al. |
| 11,224,747 B2 | 1/2022 | Bouton et al. |
| 11,318,296 B2 | 5/2022 | Xiao et al. |
| 11,318,309 B2 | 5/2022 | Marceglia et al. |
| 11,679,260 B2 | 6/2023 | Senderowicz et al. |
| 12,064,628 B2 | 8/2024 | Senderowicz et al. |
| 2001/0029391 A1 | 10/2001 | Gluckman et al. |
| 2002/0177882 A1 | 11/2002 | DiLorenzo |
| 2003/0114886 A1 | 6/2003 | Gluckman et al. |
| 2004/0073273 A1 | 4/2004 | Gluckman et al. |
| 2005/0065427 A1 | 3/2005 | Magill et al. |
| 2007/0162086 A1 | 7/2007 | DiLorenzo |
| 2007/0225674 A1 | 9/2007 | Molnar et al. |
| 2008/0183245 A1 | 7/2008 | Van Oort et al. |
| 2008/0269836 A1 | 10/2008 | Foffani et al. |
| 2009/0082829 A1* | 3/2009 | Panken ............. A61N 1/36139 607/45 |
| 2009/0099627 A1 | 4/2009 | Molnar et al. |
| 2010/0114237 A1 | 5/2010 | Giftakis et al. |
| 2010/0327887 A1 | 12/2010 | Denison et al. |
| 2011/0015702 A1* | 1/2011 | Ternes ............. A61N 1/36114 607/62 |
| 2011/0264165 A1 | 10/2011 | Molnar et al. |
| 2012/0016435 A1 | 1/2012 | Rom |
| 2013/0053722 A1 | 2/2013 | Carlson et al. |
| 2016/0242645 A1 | 8/2016 | Muller |
| 2018/0085572 A1 | 3/2018 | Stanslaski et al. |
| 2020/0220392 A1* | 7/2020 | Pan ..................... H03J 3/24 |
| 2020/0254261 A1 | 8/2020 | Arlotti et al. |
| 2021/0154476 A1 | 5/2021 | Senderowicz et al. |
| 2022/0001181 A1* | 1/2022 | Zylberberg ........ A61N 1/36078 |
| 2022/0323762 A1 | 10/2022 | Marceglia et al. |
| 2023/0285751 A1 | 9/2023 | Senderowicz et al. |

FOREIGN PATENT DOCUMENTS

| | | |
|---|---|---|
| EP | 1 940 508 B1 | 12/2011 |
| IT | MI-2015A000219 | 2/2016 |
| JP | 2005-252497 A | 9/2005 |
| JP | 2009-033303 A | 2/2009 |
| JP | 2010-517471 A | 5/2010 |
| JP | 2010-517472 A | 5/2010 |
| WO | WO-00/07494 A2 | 2/2000 |
| WO | WO-00/07494 A3 | 2/2000 |
| WO | WO-2007/049105 A1 | 5/2007 |
| WO | WO-2013/123112 A1 | 8/2013 |
| WO | WO-2014/116850 A1 | 7/2014 |
| WO | WO-2015/069797 A1 | 5/2015 |
| WO | WO-2016/132258 A1 | 8/2016 |
| WO | WO-2018/017463 A1 | 1/2018 |
| WO | WO-2018/064193 A1 | 4/2018 |
| WO | WO-2018/064225 A1 | 4/2018 |
| WO | WO-2018/112164 A1 | 6/2018 |
| WO | WO-2018/160271 A1 | 9/2018 |
| WO | WO-2018/187080 A1 | 10/2018 |
| WO | WO-2019/073341 A1 | 4/2019 |
| WO | WO-2019/153094 A1 | 8/2019 |
| WO | WO-2020/086119 A1 | 4/2020 |
| WO | WO-2020/087135 A1 | 5/2020 |
| WO | WO-2021/127379 A1 | 6/2021 |
| WO | WO-2021/138543 A1 | 7/2021 |
| WO | WO-2021/141814 A1 | 7/2021 |
| WO | WO-2021/167946 A1 | 8/2021 |
| WO | WO-2022/029445 A1 | 2/2022 |

OTHER PUBLICATIONS

Ratri Mukherjee et al., Prediction of Disorder of Brain using EEG Signal Processing in MATLAB GUI Platform, Dec. 27-29, 2017, 2nd International Conference on Electrical & Electronic Engineering (ICEEE) (Year: 2017).*

Non-Final Office Action mailed on Dec. 21, 2023, for U.S. Appl. No. 18/320,100, filed May 18, 2023, 12 pages.

Non-Final Office Action mailed on Feb. 20, 2024, for U.S. Appl. No. 16/792,098, filed Feb. 14, 2020, 15 pages.

(56) References Cited

OTHER PUBLICATIONS

Notice of Allowance mailed on Apr. 15, 2024, for U.S. Appl. No. 18/320,100, filed May 18, 2023, 8 pages.
BioWorld MedTech (2019). Cortera Wand Technology, Clarivate Analytics, 10 total pages.
BioWorld MedTech (2018). UCSF Using Closed Loop Adaptive DBS, Clarivate Analytics, 24 total pages.
Bronstein, J.M. et al. (2011). "Deep Brain Stimulation for Parkinson Disease," Archives of Neurology 68:165-171.
Brown, P. et al. (2005). "Basal Ganglia Local Field Potential Activity: Character and Functional Significance in the Human," Clinical Neurophysiology 116:2510-2519.
Brown, P. et al. (2001). "Dopamine Dependency of Oscillations Between Subthalamic Nucleus and Palladium in Parkinson's Disease," J. Neurosci. 21:1033-1038.
Brown, P. (2003). "Oscillatory Nature of Human Basal Ganglia Activity; Relationship to the Pathophysiology of Parkinson's Disease," Mov. Disord. 18:357-363.
Burgess, J.G. et al. (2010). "Identifying Tremor-Related Characteristics of Basal Ganglia Nuclei During Movement in the Parkinsonian Patient," Parkinsonism & Related Disorders 16:671-675.
Cassidy, M. et al. (2002). "Movement-Related Changes in Synchronization in the Human Basal Ganglia," Brain 125:1235-1246.
Chang, S.Y. et al. (2013). "Development of the Mayo Investigational Neuromodulation Control System: Toward a Closed-Loop Electrochemical Feedback System for Deep Brain Stimulation," Journal of Neurosurgery 119:1556-1565.
Cogan, S.F. (2008). "Neural stimulation and recording electrodes," Annu Rev Biomed Eng. 10:275-309.
De Hemptinne, C. et al. (2015). "Therapeutic Deep Brain Stimulation Reduces Cortical Phase-Amplitude Coupling in Parkinson's Disease," Nature Neuroscience 18:779-786.
Denison, T. et al. (2007). "A 2 µW 100 nV/rtHz chopper-stabilized instrumentation amplifier for chronic measurement of neural filed potentials," IEEE J. of Solid-State Circuits 42:2934-2945.
Doyle, L.M.F. et al. (2005). "Levodopa-Induced Modulation of Subthalamic Beta Oscillations During Self-Paced Movements in Patients with Parkinson's Disease," Eur. J. Neurosci. 21:1403-1412.
Eusebio, A et al. (2011). "Deep Brain Stimulation Can Suppress Pathological Synchronisation in Parkinsonian Patients," J. of Neurol. Neurosurgery & Psychiatry 82:569-573.
Foffani, G. et al. (2003). "300-HZ Subthalamic Oscillations in Parkinson's Disease," Brain 126:2153-2163.
Foffani, G. et al. (2004). "Adaptive Autoregressive Identification with Spectral Power Decomposition for Studying Movement-Related Activity in Scalp EEG Signals and Basal Ganglia Local Field Potentials," J. Neural Eng. 1:165-173.
Foffani, G. et al. (2005). "Physiological Recordings from Electrodes Implanted in the Basal Ganglia for Deep Brain Stimulation in Parkinson's Disease. The Relevance of Fast Subthalamic Rhythms," Acta Neurochir. Suppl. 93:97-99.
Foffani, G. et al. (2005). "Altered Subthalamo-Pallidal Synchronisation in Parkinsonian Dyskinesias," J. Neural Neurosurg. Psychiatry 76:426-428.
Foffani, G. et al. (2005). "Movement-Related Frequency Modulation of Beta Oscillatory Activity in the Human Subthalamic Nucleus," J. Physiol. 568:699-711.
Fogelson, N. et al. (2005). "Reciprocal Interactions Between Oscillatory Activi-ties of Different Frequencies in the Subthalamic Region of Patients with Parkinson's Disease," Eur. J. Neurosci. 22:257-266.
Gui Yun et al. (Oct. 2013). "A multi-channel fully differential programmable integrated circuit for neural recording application," J. Semicond. 34:105009-1-8.
Hamani, C. et al. (2005). "Bilateral subthalamic nucleus stimulation for Parkinson's disease: A systematic review of the clinical literature," Neurosurgery 56:1313-1321.
International Search Report mailed on May 16, 2019, for PCT Application No. PCT/IB2019/051428, filed on Feb. 21, 2019, 3 pages.

International Search Report mailed on Jan. 28, 2022, for PCT Application No. PCT/IB2021/056435, filed on Jul. 16, 2021, 6 pages.
International Search Report mailed on May 18, 2016, for PCT Application No. PCT/IB2016/050735. filed on Feb. 11, 2016, 7 pages.
Kühn, A.A. et al. (2009). "Pathological Synchronisation in the Subthalamic Nucleus of Patients with Parkinson's Disease Relates to Both Bradykinesia and Rigidity," Exp. Neurology 215:380-387.
Kühn, A.A. et al. (2005). "The Relationship Between Local Field Potential and Neuronal Discharge in the Subthalamic Nucleus of Patients with Parkinson's Disease," Experimental Neurology 194:212-220.
Kühn, A.A. et al. (2004). "Event-Related Beta Desynchronization in Human Subthalamic Nucleus Correlates with Motor Performance," Brain 127:735-746.
Kuncel, A.M. et al. (2004). "Selection of stimulus parameters for deep brain stimulation," Clin. Neurophysiol. 115:2431-2441.
Levy, R. et al. (2002). "Dependence of Subthalamic Nucleus Oscillations on Movement and Dopamine in Parkinson's Disease," Brain 125:1196-1209.
Limousin, P. et al. (1996). "Abnormal Involuntary Movements Induced by Subthalamic Nucleus Stimulation in Parkinsonian Patients," Movement Disorders 11:231-235.
Lin, Y.P. et al. (2016). "A Battery-Less, Implantable Neuro-Electronic Interface for Studying the Mechanisms of Deep Brain Stimulation in Rat Models," IEEE Trans. Biomed. Circuits Syst. 10:98-112.
Modolo, J. et al. (2010). "Past, present and future of bran stimulation," Mathematical modelling of Natural Phenomena 5:185-207.
Modolo, J. et al. (2010). "Model-driven therapeutic treatment of neurological disorders: Reshaping brain rhythms with neuromodulation," Interface Focus 1:61-74.
Moro, E. et al. (2006). "Subthalamic Nucleus Stimulation: Improvements in Outcome with Reprogramming," Archives of Neurol. 63:1266-1272.
Non-Final Office Action mailed on May 18, 2022, for U.S. Appl. No. 17/165,124, filed Feb. 2, 2021, 9 pages.
Notice of Allowance mailed on Nov. 14, 2019, for U.S. Appl. No. 15/550,284, filed Aug. 10, 2017, 7 pages.
Notice of Allowance mailed on Jun. 17, 2020, for U.S. Appl. No. 16/282,167, filed Feb. 21, 2019, 8 pages.
Notice of Allowance mailed on Dec. 17, 2021, for U.S. Appl. No. 16/706,552, filed Dec. 6, 2019, 8 pages.
Notice of Allowance mailed on Oct. 31, 2022, for U.S. Appl. No. 17/165,124, filed Feb. 2, 2021, 9 pages.
Notice of Allowance mailed on Feb. 21, 2023, for U.S. Appl. No. 17/165,124, filed Feb. 2, 2021, 9 pages.
Pedram, A. et al. (2013). "A translational platform for prototyping closed-loop neuromodulation systems," Frontiers in Neural Circuits 6:117.
Priori, A et al. (2004). "Rhythm-Specific Pharmacological Modulation of Subthalamic Activity in Parkinson's Disease," Experimental Neurology 189:369-379.
Priori, A et al. (2013). "Adaptive Deep Brain Stimulation (aDBS) Controlled by Local Field Potential Oscillations," Experimental Neurology 245:77-86.
Priori, et al, "Movement-Related Modulation of Neural Activity in Human Basal Ganglia and its L-Dopa Dependency: Recordings from Deep Brain Stimulation Electrodes in Patients with Parkinson's Disease", Neurol. Sci., Sep. 2002, pp. S101-S102.
Qian, X. et al. (2017). "A Method for Removal of Deep Brain Stimulation Artifact from Local Field Potentials," IEEE Trans. on Neural Systems and Rehabilitation Engineering, 25(12), 2217-2226.
Rosin, B. et al. (2011). "Closed-Loop Deep Brain Stimulation Is Superior in Ameliorating Parkinsonism," Neuron 72:370-384.
Santaniello, S. et al. (2011). "Closed-Loop Control of Deep Brain Stimulation: A Simulation Study," IEEE Transactions on Neural Systems and Rehabilitation Engineering 19:15-24.
Silberstein, P. et al. (2003). "Patterning of Globus Pallidus Local Field Poten-tials Differs Between Parkinson's Disease and Dystonia," Brain 126:2597-2608.

(56) References Cited

OTHER PUBLICATIONS

Stanslaski, S. et al. (2011). "Design and validation of a fully implantable, chronic, closed-loop neuromodulation device with concurrent sensing and stimulation," IEEE Trans Neural Syst Rehabil Eng. 20:410-421.

Williams, D. et al. (2002). "Dopamine-Dependent Changes in the Functional Connectivity Between Basal Ganglia and Cerebral Cortex in Humans," Brain 125:1558-1569.

Written Opinion of the International Searching Authority mailed on May 16, 2019, for PCT Application No. PCT/IB2019/051428, filed on Feb. 21, 2019, 5 pages.

Written Opinion of the International Searching Authority mailed on Jan. 28, 2022, for PCT Application No. PCT/IB2021/056435, filed on Jul. 16, 2021, 13 pages.

Written Opinion of the International Searching Authority mailed on May 18, 2016, for PCT Application No. PCT/IB2016/050735, filed on Feb. 11, 2016, 8 pages.

Yoshida, F. et al. (2010). "Value of Subthalamic Nucleus Local Field Potentials Recordings in Predicting Stimulation Parameters for Deep Brain Stimulation in Parkinson's Disease," Journal of Neurology, Neurosurgery & Psychiatry 81:885-889.

Zhao-Hui, W. et al. (2015). "Implantable analog front-end with high PSRR and CMRR for neural signal acquisition," Journal of South China University of Technology (Natural Science Edition) 43:15-20 (English Abstract Provided).

Zhou, A. et al. (2019). "A wireless and artefact-free 128-channel neuromodulation device for closed-loop stimulation and recording in non-human primates," Nature Biomedical Engin. 3:15-26.

Zhou, A. et al. (2017). WAND: A 128-channel, closed-loop, wireless artifact-free neuromodulation device, 30 total pages.

Extended European Search Report mailed on Dec. 14, 2020, for EP Application No. 20 196584.5, filed on Feb. 11, 2016, 9 pages.

Final Office Action mailed on Jul. 24, 2024, for U.S. Appl. No. 16/792,098, filed Feb. 14, 2020, 14 pages.

Non-Final Office Action mailed on Aug. 19, 2024, for U.S. Appl. No. 17/706,378, filed Mar. 28, 2022, 13 pages.

\* cited by examiner

1100

Check impedance of a set of electrode pairs and excluding a subset of electrode pairs from the set of electrode pairs that have aberrant impedance values  1101

Screen power spectrum of a set of neural activates on the remaining electrode pairs  1102

Titrate a therapeutic window and defining a $A_{max}$ and $A_{min}$  1103

Select electrode pairs for sensing and showing a highest beta activity excluding the stimulation electrodes  1104

Extract a plurality of spectral features of the plurality of neural signal records for a predetermined number of days 1201

Select a plurality of selected spectral features within a frequency band of the plurality of spectral features 1202

Generate an average of the plurality of selected spectral features within the frequency band and across the predetermined number of days 1203

Select a plurality of medication-on time intervals and a plurality of medication-off time intervals during the predetermined number of days 1204

Generate a minimum average of the plurality of selected spectral features within the frequency band and within the plurality of medication-on time intervals 1205

Generate a maximum average of the plurality of selected spectral features within the frequency band and within the plurality of medication-off time intervals 1206

FIG. 12

SYSTEMS AND METHODS FOR ADAPTIVE DEEP BRAIN STIMULATION

CROSS REFERENCE TO RELATED APPLICATIONS

This application claims priority to U.S. provisional patent application No. 63/053,263, filed on Jul. 17, 2020, the contents of which are incorporated herein by reference in its entirety.

TECHNICAL FIELD

The present disclosure generally relates to the field of deep brain stimulation, and in particular to methods and devices that enable data communication and data storage for adaptive deep brain stimulation systems.

BACKGROUND

Deep brain stimulation (DBS) systems are used in various industries including medical diagnostics or medical treatments, due to number of advantages. For example, deep brain stimulation can deliver electrical stimulation to neural structures of the central nervous system of a patient to modulate neural activity. Neural activities of the patient can be also studied in conjunction with the deep brain stimulation. Deep brain stimulation devices implanted into a biological tissue, however, are usually compact for safety reasons as well as for the comfort of the patient and therefore have limited power capacity, data processing, data storage, and communication interface capabilities at dispose for operation. Moreover, conventional deep brain stimulation are often programmed by a physician for a predefined stimulation setting. Each patient, however, often show symptoms, neural activity peaks, and neural activity frequency bands that are different from a norm. Such patients could benefit from an adaptive and patient-specific calibration. Due to the aforementioned limitation in power capacity, data processing, data storage, and communication interface capabilities in known deep brain stimulation systems, providing effective and efficient adaptive deep brain stimulation remains a quest. Thus, there is a need for new and improved systems and methods for deep brain stimulation.

SUMMARY

Generally, in some variations, a system for deep brain stimulation may include an implantable device that acquires and stores neural activity signal records and applies electrical stimulation. The system may further include a personal controller device that establishes a first wireless connection (e.g., a Bluetooth communication) to the implantable device. The personal controller device may transmit power to the implantable device, and the implantable device may transmit the neural activity signal records to the personal controller device over the first wireless connection. The system may further include a clinician programmer device that receives the neural activity signal records from the implantable device by establishing a second wireless connection based on activation of the first wireless connection. The clinician programmer device sets stimulation parameters based on the neural activity signal records. The clinician programmer device further establishes a second wireless connection (e.g., industrial, scientific and medical (ISM) communication, short-range device (SRD) communication, and/or the like) to the implantable device based on the activation of the first wireless connection (e.g., upon authentication of a user-entered personal identification number).

In some implementations, the power may be inductive power induced to the implantable device. In some implementations, the neural activity signal records may be transmitted by the implantable device to the personal controller device automatically during the recharging process and/or on demand.

The personal controller device generally includes a first unit and a second unit. The first unit may be removably connected to the second unit and provide power to the second unit when connected to the second unit. The first unit may include a memory (e.g., a solid-state memory) that stores the neural activity signal records. The personal controller may be configured further to display an indication of a remaining power status of the implantable device or an indication of a treatment mode of the implantable device. In some variations, the personal controller may receive a signal to change the treatment mode of the implantable device.

The clinician programmer device may include a custom designed programmable electronic device, a smartphone, tablet, and/or a personal compute device. In some instances, the stimulation parameters are first stimulation parameters and the treatment mode is a first treatment mode. The clinician programmer device may be configured to generate a second treatment mode and second stimulation parameters. The clinician programmer device may further transmit the second treatment mode and the second stimulation parameters to the implantable device.

The system may further include a user compute device having an application. The user compute device may be configured to receive patient log data and the neural activity signal records. In some instances, the patient log data can be recorded and/or received from the implantable device and/or the personal controller device. The user compute device may associate the patient log data and the neural activity signal records based on at least a time correlation between the patient log data and the neural activity signal records. The user compute device may further determine medication-on time intervals and/or medication-off time intervals based on the neural activity signal records and the patient log data. The user compute device may further generate the stimulation parameters according to the neural activity signal records during the medication-on time intervals and the medication-off time intervals. In some instances, the medication-on time intervals and the medication-off time intervals may be determined by a user of the user compute device (e.g., physician, clinician, etc.). In some instances, the user may determine a threshold for categorizing time intervals to medication-on time interval and medication-off time intervals. For example, time intervals in which the neural activity signals records have an amplitude larger than threshold may be categorized as a medication-off time interval.

In some implementations, the user compute device may include a smartphone, a tablet, a personal compute device, and/or the like. The user compute device and/or the clinician programmer device may generate and display a plot of the neural activity signal records or a statistical distribution of the neural activity signal records.

The user compute device may be further configured to extract spectral features within a frequency band of the neural activity signal records that are recorded during a predefined time period. The user compute device may determine medication-on time intervals and medication-off time intervals during the predefined time period. The user compute device may further generate a first average value of the spectral features within the medication-on time intervals of the frequency band and a second average value of the spectral features within the medication-off time intervals of the frequency band. The user compute device may generate the stimulation parameters based on the first average value and the second average value. The frequency band may be a low-frequency band, the alpha frequency band, or the beta frequency band and gamma frequencies.

In some variations, the stimulation parameters may include at least one of a stimulation frequency, a stimulation pulse width, a stimulation amplitude, an upper neural activity signal threshold, and/or a lower neural activity signal threshold.

In some implementations, the neural activity signal records and the patient log data may be time recorded. The neural activity signal records may include local field potential records (e.g., from both brain hemispheres) in a low-frequency band, the alpha frequency band, the beta frequency band, and/or gamma frequencies. The local field potentials may include electrical field potentials, electromagnetic field potentials, magnetic field potentials, and/or other suitable field potentials. In some variations, the neural activity signal records and log data may be recorded and stored continuously by the implantable device. In some variations, the neural activity signal records and log data are recorded and stored at discrete time intervals by the implantable device.

The user compute device and/or the clinician programmer device may regularly transmit the neural activity signal records and/or patient log data or the stimulation parameters to a biobank server. In some instances, the user compute device and/or the clinician programmer device may delete the neural activity signal records and/or patient log data or the stimulation parameters from a memory of the user compute device and/or the clinician programmer device. Clearing the memory on a regular basis can be advantageous to reduce memory usage of the user compute device and/or the clinician programmer device.

In some variations, the clinician programmer device may establish an authenticated communication channel with the personal controller device. The personal controller device may transmit the stimulation parameters (received from the clinician programmer device) to the implantable device. The personal controller device may further be configured to display an indication of a remaining power status of the implantable device or an indication of a treatment mode of the implantable device. The stimulation parameters include at least one of a stimulation frequency, a stimulation pulse width, a stimulation amplitude, an upper neural activity signal threshold, and/or a lower neural activity signal threshold.

The clinician programmer device may receive patient log data from a user compute device and associate the patient log data and the neural activity signal records based on at least a time correlation between the patient log data and the neural activity signal records. The neural activity signal records may include local field potential records in a low-frequency band, the alpha frequency band, the beta frequency band, and/or gamma frequencies. The clinician programmer device may then determine medication-on time intervals and medication-off time intervals based on the neural activity signal records and the patient log data received from the user compute device. The clinician programmer device may be configured to further generate the stimulation parameters according to the neural activity signal records during the medication-on time intervals and the medication-off time intervals.

In some instances, the stimulation parameters are first stimulation parameters and the treatment mode is a first treatment mode. The clinician programmer device may be configured to generate a second treatment mode and second stimulation parameters and transmit the second treatment mode and the second stimulation parameters to the personal controller device. The personal controller device can then transmit the second stimulation parameters and the second treatment to the implantable device.

The clinician programmer device may be further configured to extract spectral features within a frequency band of the neural activity signal records that are recorded during a predefined time period. The clinician programmer device may determine medication-on time intervals and medication-off time intervals during the predefined time period. The clinician programmer device may further generate a first average value of the spectral features within the medication-on time intervals of the frequency band and a second average value of the spectral features within the medication-off time intervals of the frequency band. The clinician programmer device may generate the stimulation parameters based on the first average value and the second average value.

In some implementation, the user compute device and/or the clinician programmer device may be configured to train a machine learning model based on historical neural activity signal records or a set of historical stimulation parameters. Once the machine learning model is trained, the user compute device and/or the clinician programmer device may identify the stimulation parameters by executing the machine learning model based on the neural activity signal records.

Generally, in some variations, a method for deep brain stimulation may include receiving neural activity signal records acquired over a predefined time period. The neural activity signal records may be acquired by an implantable device and the predefined time period may be one day, 5 days, 10 days, and/or the like. The method may further include mapping neural activity signal records with medication-on and medication-off time intervals that have been determined based on patient log data. The method may further include extracting spectral features within a frequency band of the neural activity signal records. The spectral features within the frequency band may include values of the spectral feature for time intervals within the predefined time period. The method may further include generating a first average value of the spectral features within the medication-on time intervals of the frequency band over the predefined time period, and a second average value of the spectral features within the medication-off time intervals of the frequency band over the predefined time period. The method may further include generating stimulation parameters based on the first average value and the second average value.

The method for deep brain stimulation may include measuring a set of impedance values of a first set of electrodes. For example, the measuring of the set of impedance values is performed at a medication-off period. The method may further include comparing the set of impedance values with a permitted impedance range to identify a second set of electrodes having impedance values within the permitted impedance range. The method may further include screening a set of neural activity signal records of a patient using the second set of electrodes. The method may further include selecting a third set of electrodes showing highest neural activity signal records from the set of neural activity signal records.

In some implementations, the method may further include defining a minimum stimulation amplitude $A_{MIN}$ eliciting a detectable clinical benefit to the patient and a maximum stimulation amplitude $A_{MAX}$ before eliciting a side effect to the patient. The stimulation parameters may include the minimum stimulation amplitude $A_{MIN}$ and/or the maximum stimulation amplitude $A_{MAX}$. The first average value may include a minimum beta frequency band power value $P_{\beta MIN}$, and/or the second average value may include a maximum beta frequency band power value $P_{\beta MAX}$.

In some implementations, the stimulation parameters may collectively define brain stimulation (DBS) amplitudes $V_{DBS}$. The DBS amplitudes may be generally defined by:

$$V_{DBS} = \frac{P_\beta - P_{\beta MIN}}{P_{\beta MAX} - P_{\beta MIN}} * (A_{MAX} - A_{MIN}) + A_{MIN}$$

where $P_\beta$ is the power of the beta frequency band of the neural activity signal record.

In some implementations, the method may further include determining a peak frequency of the neural activity signal records within the frequency band and selecting a patient-specific frequency band based on the peak frequency. The method may further include, delivering electrical stimulations according to the stimulation parameters to stimulate neural tissue using an implantable device.

In some implementations, the neural activity signal records may be generally acquired by an implantable device. The predefined time period may be determined based on an indication of a measured remaining power of the implantable device, or determined based on an indication of remaining memory of the implantable device. The method may further include transmitting the indication of the measured remaining power or the indication of remaining memory of the implantable device to a personal controller device such that the indication of the remaining power or the indication of remaining memory are displayed, via a user interface, to a user of the personal controller device.

BRIEF DESCRIPTION OF THE DRAWINGS

FIG. 11 is an exemplary method for selecting a set of sensing electrodes, a set of stimulation electrodes, and power bands.

FIG. 12 is an exemplary method for adaptive deep brain stimulation.

DETAILED DESCRIPTION

Non-limiting examples of various aspects and variations of the invention are described herein and illustrated in the accompanying drawings.

Described herein are exemplary deep brain stimulation systems and methods that are suitable for highly reliable and secure deep brain stimulation. The deep brain stimulation systems and methods described herein include an implantable device, a patient personal controller device, a user compute device, and/or a clinician programmer device that can be communicatively coupled to each other to communicate and process data for an adaptive deep brain stimulation or a conventional deep brain stimulation.

One or more deep brain stimulation systems described herein may record, store, communicate, and analyze neural activity signal records of a patient for an effective and efficient adaptive deep brain stimulation. Moreover, the one or more deep brain stimulation systems provide adaptive deep brain stimulation (aDBS) by changing stimulation parameters of the patient in real-time based on the neural activity signal records. Real-time recording, communication, and/or analysis of the patient's neural activity signal records and aDBS, compared to conventional deep brain stimulation (cDBS), may significantly improve clinical outcome of the one or more deep brain stimulation systems described herein. Use of aDBS with the one or more deep brain stimulation systems described herein may enable more time-oriented improvement/optimization of stimulation parameters that may potentially lead to new treatment methods and findings about a condition(s) of the patient.

Figure 1:
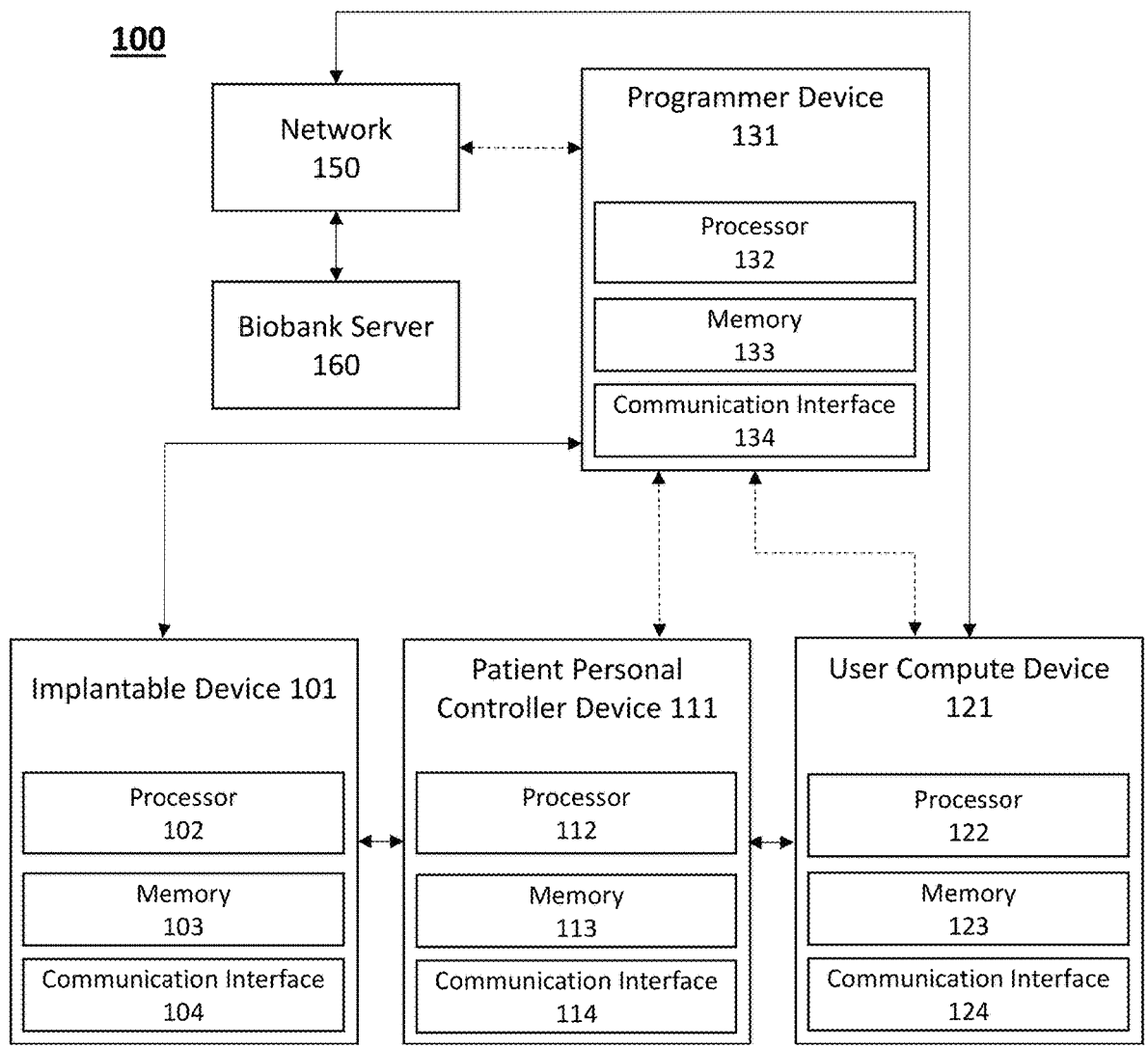
FIG. 1 is a block diagram of an exemplary deep brain stimulation system.

Deep Brain Stimulation (DBS) System and Data Flow Between Various Devices of the DBS System FIG. 1 is a block diagram of an exemplary deep brain stimulation system 100. The deep brain stimulation system 100 includes an implantable device 101 (also referred to herein as an 'implantable pulse generator (IPG) device'), a patient personal controller device 111, a user compute device 121 (also referred to herein as an 'app'), and a clinician programmer device 131 (also referred to herein as a 'programmer device'). The implantable device 101 is operatively coupled to the patient personal controller device 111 and the clinician programmer device. The patient personal controller device 111 is operatively coupled to the user compute device 121 and, in some implementations, may be further operatively coupled to the clinician programmer device 131. In some implementations, the user compute device may be operatively coupled to the programmer device 131. The brain stimulation system 100 may be used to provide deep brain stimulation to a patient by collecting data from the patient, and communicating/analyzing the data between/using the implantable device 101, the patient personal controller device 111, the user compute device 121, and/or the clinician programmer device 131 to effectively use storage and processing power of each. The user compute device 121 is connected to or operatively coupled to a biobank server 160 via a network 150. Alternatively, or in addition, in some implementations, the clinician programmer device 131 may be connected or operatively coupled to the biobank server 160 via the network 150.

The patient personal controller device 111, the user compute device 121, and/or the clinician programmer device 131 each may include a hardware-based computing device and/or multimedia device, such as, for example, a smartphone, a tablet, a wearable device, a desktop computer, a laptop, a custom-built compute device, and/or the like. Moreover, each of the patient personal controller device 111, the user compute device 121, and/or the clinician programmer device 131 may be powered by a plug-in and/or include a re-chargeable battery. The implantable device 101 may be powered by a re-chargeable battery that may be powered by direct electrical connection and/or induction.

The implantable device 101 described herein is an implantable and rechargeable neurostimulator that may be operatively coupled to patient personal controller device 111 for initialization and/or to the clinician programmer device 131 for programming. The implantable device 101 includes a processor 102, a memory 103, and a communication interface 104, and can be implanted in a patient to record, store, and/or analyze a set of neural activity signal records and/or further provide a set of stimulations based on a set of stimulation parameters to the patient. In some variations, the implantable device can further include a battery to store power and/or a set of connectors (e.g., octapolar connectors). The implantable device 101 can connect to a deep brain stimulation (DBS) probe extensions. The implantable device 101 can provide, via the probe extensions, an adaptive DBS (aDBS) and/or a conventional DBS (cDBS) to a patient.

The processor 102 can include, for example, a hardware based integrated circuit (IC) or any other suitable processing device configured to run or execute a set of instructions or a set of codes. For example, the processor 102 can include a general purpose processor, a central processing unit (CPU), an accelerated processing unit (APU), an application specific integrated circuit (ASIC), and/or the like. The processor 102 is operatively coupled to the memory 103 through a system bus (for example, address bus, data bus, and/or control bus, not shown). The processor 102 is operatively coupled to the memory 103 via a system bus (for example, address bus, data bus, and/or control bus, not shown). In some variations, the processor 102 can include and/or be operatively coupled to a Vstim generator(s), a diagnostic device(s), a current controller(s), a waveform generator(s), an impedance measurement device(s), a signal processing controller(s), and/or the like.

The memory 103 of the implantable device 101 can be, for example, a memory buffer, a random access memory (RAM), a read-only memory (ROM), a flash drive, a secure digital (SD) memory card, an embedded multi-time programmable (MTP) memory, an embedded multi-media card (eMMC), a universal flash storage (UFS) device, and/or the like. The memory 103 can store, for example, one or more code that includes instructions to cause the processor 102 to perform one or more processes or functions (e.g., recording the set of neural activity signal records, generating a set of pulse signals, and/or the like).

The communication interface 104 of the implantable device 101 can be a hardware component of the first compute device 101 operatively coupled to the processor 102 and/or the memory 103. The communication interface 104 can be operatively coupled to and used by the processor 102. The communication interface 104 can be, for example, a network interface card (NIC), a Wi-Fi™ module, a Bluetooth® module, an optical communication module, and/or any other suitable wired and/or wireless communication interface (i.e., Wireless Medical Telemetry Service (WMTS); Medical Device Radio communication Service (MedRadio), Medical Implant Communications Service (MICS), Medical Micropower Network (MNN), Medical Body Area Network (MBAN), and/or the like). The communication interface 104 can be configured to connect the implantable device 101 to the patient personal controller device 111, the user compute device 121, and/or the clinician programmer device 131, as described in further detail herein. In some instances, the communication interface 104 can facilitate receiving and/or transmitting the set of neural activity signal records and/or a set of stimulation parameters to/from the patient personal controller device 111, the user compute device 121, and/or the clinician programmer device 131, each communicatively coupled to the implantable device 101. In some instances, data received via communication interface 104 can be processed by the processor 102 or stored in the memory 103, as described in further detail herein.

The patient personal controller device 111 described herein may establish a first wireless connection (an RF wireless connection) to the implantable device 101 and/or provide power (inductive electrical power, radio frequency (RF) power harvesting, and/or the like) to the implantable device 101 for operation. The patient personal controller device 111 may receive/transmit data (e.g., the neural activity signal records, the set of stimulation parameters, and/or the like) to the implantable device 101 via the first wireless connection. The patient personal controller device 111 includes a processor 112, a memory 113, and a communication interface 114 which can be structurally and/or functionally similar to the processor 102, the memory 103, and the communication interface 104, respectively. In some instances, the patient personal controller device 111 may receive, via the communication interface 114, the set of neural activity signal records from the implantable device 101 and store the set of neural activity signal records in the memory 113. In some variations, the patient personal controller device 111 may include a first component and a second component each having a processor, a memory, and a communication interface structurally and/or functionally similar to the processor 102, the memory 103, and the communication interface 104, respectively. The first component may be used to recharge the implantable device 101 and the second component may be used to connect and provide power to the first component.

The user compute device 121 includes a processor 122, a memory 123, and a communication interface 124 which can be structurally and/or functionally similar to the processor 102, the memory 103, and the communication interface 104, respectively. In some instances, the user compute device 121 may be a personal device such as a cell phone, a tablet, a compute device, a watch, a virtual reality device, and/or the like. The user compute device 121 may include an application (not shown) as a software received from the communication interface 124, stored in the memory 123, and executed by the processor 122. For example, a code to cause the processor to analyze the set of neural activity data records. Alternatively, the application can be a hardware-based device that can be attached to the user compute device 121. For example, an integrated circuit (IC) that can cause the user compute device 121 to analyze the set of neural activity data records.

The user compute device 121 described herein may connect and/or operatively couple to the patient personal controller device 111 to receive and/or transmit data including the neural activity signal records. In some instances, the user compute device 121 may receive and store patient log data. The patient log data can be received from the patient personal controller device 111 and/or a user (e.g., a patient, a guardian of the patient, an artificial intelligence personal assistant of the patient, and/or the like) of the user compute device 121, and may include, for example, a sequential/chronological description of events (e.g., hourly, daily, weekly, and/or the like), a medication consumption history, and/or the like.

The application of the user compute device 121 may associate the patient log data and the neural activity signal records based on at least a time correlation between the patient log data and the neural activity signal records. The user compute device 121 may further determine a set of medication-on time intervals and a set of medication-off time intervals based on the neural activity signal records and the patient log data. The application may further generate the stimulation parameters based on the neural activity signal records during the set of medication-on time intervals and the medication-off time intervals.

In some variations, the application may be included/implemented in the patient personal controller device 111 and/or the clinician programmer device 131. For example, the patient personal control 111 may receive data including the set of neural activity data records from the implantable device 101 and the patient log data from the user of the patient personal controller device 111. The patient personal control 111 may then determine the set of medication-on time intervals and the medication-off time intervals based on the set of neural activity data records and the patient log data. In some variations, the application may be implemented in a web service provider and be accessed via an application programming interface (API) downloaded in and/or installed to the user device 121, the patient personal controller device 111, and/or the clinician programmer device 131.

The clinician programmer device 131 includes a processor 132, a memory 133, and a communication interface 134 which can be structurally and/or functionally similar to the processor 102, the memory 103, and the communication interface 104, respectively. The clinician programmer device 131 may establish a second wireless connection (an RF wireless connection) to the implantable device 101 based on the activation of the first wireless connection. The clinician programmer device 131 can store and analyze the set of neural activity signal records to provide stimulation/treatment modes (i.e., cDBS treatment plan modes, aDBS treatment modes) to the implantable device 101. The clinician programmer device can be used to program the implantable device 101. The clinician programmable device 131 can be connected or operatively coupled (e.g., via a radio frequency (RF) communication protocol at 2.5 GHz) to the implantable device 101 to receive the set of neural activity signal records from the implantable device 101 and/or transmit the set of stimulation parameters to the implantable device 101.

In one example, the implantable device 101 can include at a first time a first set of stimulation parameters and a first treatment mode and record a set of neural activity signal records (e.g., local field potentials (LFP)). The first treatment mode can include, for example, a time table to provide the stimulations based on the first stimulation parameters. The implantable device 101 can transmit the set of neural activity signal records to the clinician programmer device 131. A clinician (e.g., a doctor, a nurse, and/or the like) using the clinician programmer device 131 can then determine and/or provide a second set of stimulation parameters and/or a second treatment mode based on the set of neural activity signal records received from the implantable device 101. The clinician programmer device 131 can transmit the second treatment mode and/or the second set of stimulation parameters to the implantable device 101.

In some implementations, the second wireless connection can be an authenticated wireless connection. For example, the second wireless connection can be established only after a user of the clinician programmer device 131 enters a personal identification number (PIN). In some instances, the authentication of the second wireless connection happen after the implantable device 101 and the clinician programmer device 131 exchange a key(s).

In some variations, the clinician programmer device 131 may receive the neural activity signal records from the implantable device 101 based on activation of the first wireless connection and without establishing the second wireless connection with the implantable device 101. In such variations, the clinician programmer device 131 may provide treatment modes to the implantable device 101 via the patient personal controller device 111.

In some variations, the clinician programmer device 131 may be connected and/or operatively coupled to a clinician external device for impedance measurement of externalized probe extensions in an operation room. The impedance measurement can involve measuring electrical resistance, capacitance, inductance, and/or the like. The clinician programmer device 131 can further format the impedance values by normalizing them into a common/standardized scale, analyze the impedance values, and/or display the impedance values to the user of the clinician programmer device 131.

The network 150 can be a digital telecommunication network of servers and/or compute devices. The servers and/or compute devices on the network can be connected via one or more wired or wireless communication networks (not shown) to share resources such as, for example, data storage, connectivity service, and/or computing power. The wired or wireless communication networks between servers and/or compute devices of the network 150 can include one or more communication channels, for example, a radio frequency (RF) communication channel(s), an extremely low frequency (ELF) communication channel(s), an ultra-low frequency (ULF) communication channel(s), a low frequency (LF) communication channel(s), a medium frequency (MF) communication channel(s), an ultra-high frequency (UHF) communication channel(s), an extremely high frequency (EHF) communication channel(s), a fiber optic commination channel(s), an electronic communication channel(s), a satellite communication channel(s), and/or the like. The network 150 can include, for example, the Internet, an intranet, a local area network (LAN), a wide area network (WAN), a metropolitan area network (MAN), a worldwide interoperability for microwave access network (WiMAX®), a virtual network, any other suitable communication system and/or a combination of such networks.

The biobank server 160 may include servers and/or compute devices that may operatively couple, via the network 150, to the user compute device 121 and/or the programmer device 131. The biobank server 160 may provide a data storage to the user compute device 121 and/or the programmer device 131. In some implementations, the biobank server 160 may, in addition to the data storage, provide a connectivity, and/or a computing service to the user compute device 121 and/or the programmer device 131. In some variations, the biobank server 160 may include and/or execute a cloud-based service such as, for example, a software as a service (SaaS), a platform as a service (PaaS), an infrastructure as a service (IaaS), and/or the like. In some instances, the biobank server 160 receives, processes, and stores the neural activity data records, the patient log data, and/or the stimulation parameters. In some implementations, the biobank server 160 generates a timestamped version of each of the set of neural activity data records, the patient log data, and/or the set of stimulation parameters before storage in a database (e.g., a Structured Query Language (SQL) database).

As shown in FIG. 1, the deep brain stimulation system 100 may include an implantable device 101 that acquires and stores neural activity signal records and applies electrical stimulation. The deep brain stimulation system 100 further includes a patient personal controller device 111 that establishes a wireless connection to the implantable device 101 to receive the neural activity signal records and recharge a battery of the implantable device 101. The patient personal controller device transmits power to the implantable device and the implantable device transmits neural activity signal records to the patient personal controller device over the wireless connection. The patient personal controller device 111 may operatively couple (e.g., a Bluetooth connection, a WiFi connection, and/or the like) to and transmits the neural activity signal records and/or the patient log data to the user compute device 121. The user compute device 121 analyzes the neural activity signal records and/or the patient log data to determine the medication-on time intervals and the medication-off time intervals based on the neural activity signal records and generate the set of stimulation parameters. The deep brain stimulation system 100 further includes a clinician programmer device 131 that establishes a second wireless connection to the implantable device 101 based on the activation of the first wireless connection, receives the neural activity signal records, and sets the stimulation parameters based on the neural activity signal records. The user compute device 121 can be further configured to connect to the network 150 via a network connection (e.g., a WiFi connection, a $5^{th}$ generation (5G) network connection, and/or the like) and transmit the neural activity signal records, the patient log data, and/or the stimulation parameters to the biobank server 160 via the network 150.

In some instances, the user compute device 121 includes a graphical user interface (GUI) and displays, via the GUI of the user compute device 121, a plot of the neural activity signal records or a statistical distribution of the neural activity signal records. The statistical distribution of the neural activity records may include for example, a moving average, daily average value, weekly average values, variance of distribution of the neural activity records, local maxima, local minima, global maxima, global minima, and/or the like.

In some instances, to determine the medication-on time intervals and the medication-off time intervals, the user compute device 121 process (e.g., extract, display, and/or the like) a set of spectral features within a frequency band of the neural activity signal records that are recorded during a predetermined time period. The frequency band may include a low-frequency band, the alpha frequency band, or the beta frequency band, the gamma frequencies, and/or the like. The user compute device 121 may further generate a first average value of the set of spectral features within the medication-on time intervals of the frequency band and a second average value of the set of spectral features within the medication-off time intervals of the frequency band. The user compute device 121 may generate the of stimulation parameters based on the first average value and the second average value.

In some implementations, a patient identification card is provided to a user of deep brain stimulation system 100. The patient identification card may include information about the user including a model of a set of devices of the deep brain stimulation system 100, a set of names of the set of devices, a set of serial numbers of the set of devices, identifying information about the patient, a date of implantation of the implantable device 101 in the user, information about the treating clinician (name, telephone number, qualifications, permission, etc.), information about manufacturer, a note whether the patient has the implantable device 101 or any other implantable devices, a note whether patient may or may not undergo diathermy, a note whether a magnetic resonance imaging (MRI) is contraindicated, general safety information, patient-specific safety information, patient's medical history, and/or the like. In some instances, the patient identification card can be stored in the implantable device 101, the patient controller device 111, and/or the application on the user compute device 121.

In some embodiments, the clinician programmer device 131 is not operatively coupled to the implantable device 101 and the patient personal controller device 111 may operatively couple (e.g., a Bluetooth connection, a WiFi connection, and/or the like) to and transmit the neural activity signal records and/or the patient log data to the clinician programmer device 131. In such embodiments, the clinician programmer device 131 analyzes the neural activity signal records and/or the patient log data to determine the medication-on time intervals and the medication-off time intervals based on the neural activity signal records and generate the set of stimulation parameters. The clinician programmer device 131 can be further configured to connect to the network 150 via a network connection (e.g., a WiFi connection, and/or the like) and transmit the neural activity signal records, the patient log data, and/or the stimulation parameters to the biobank server 160 via the network 150.

In some variations, a cDBS treatment mode can be used in addition to an aDBS treatment mode. For example, one month of monitoring/observation of neural activity data records (e.g., local field potential activities stored as numerical time series) can be stored in the patient controller and/or the implantable device 101 and then transmitted to the user compute device 121 and/or the clinician programmer device 131 for analysis. The user compute device 121 and/or the clinician programmer device 131 may then generate and transmit a set of stimulation parameters and the aDBS treatment mode to the patient controller and/or the implantable device 101 for use.

Figure 2A:
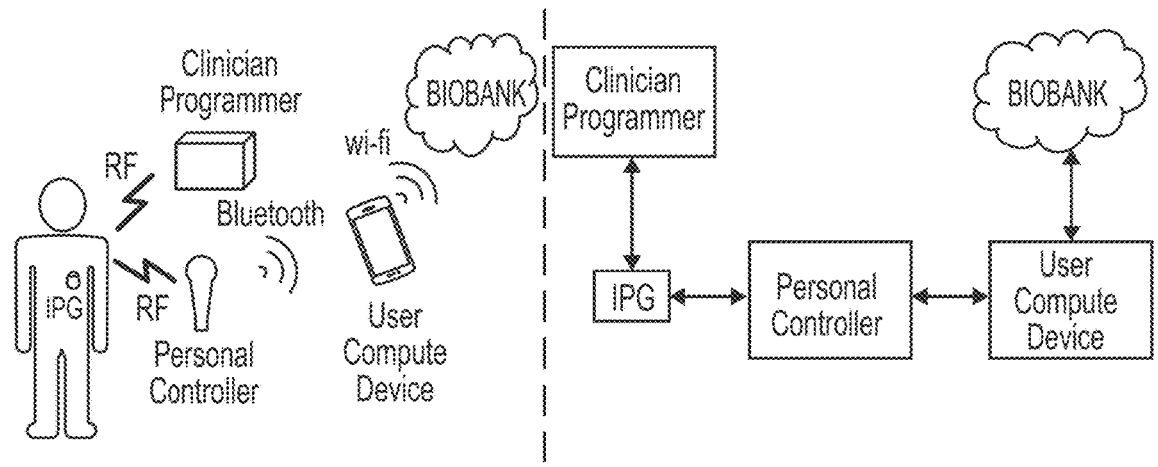
FIGS. 2A and 2B are schematic descriptions of an exemplary deep brain stimulation system.
Figure 2B:
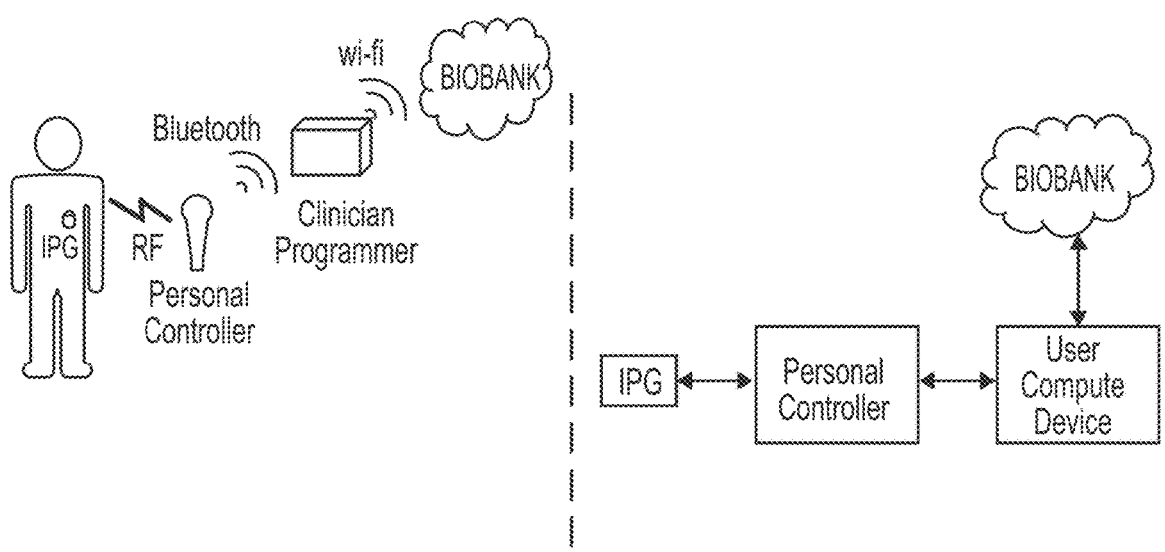

FIGS. 2A and 2B are schematic descriptions of an exemplary deep brain stimulation systems, according to some variations. As shown in FIG. 2A, a deep brain stimulation system may include an implantable device (also referred to as an IPG), a patient personal controller device (also referred to as a personal controller), a user compute device, and a clinician programmer device (also referred to as 'clinician programmer'). The IPG may acquire and store neural activity signal records of a patient and apply electrical stimulations to the patient. The personal controller establishes a wireless connection to the IPG, receive the neural activity signal records, and recharge a battery of the IPG. The personal controller transmits (e.g., via an inductive coil) power to the IPG and the IPG transmits neural activity signal records to the personal controller over the wireless connection. The personal controller may operatively couple (e.g., a Bluetooth connection, a WiFi connection, and/or the like) to and transmits the neural activity signal records and/or the patient log data to a user compute device. The user compute device analyzes the neural activity signal records and/or the patient log data to determine the medication-on time intervals and the medication-off time intervals based on the neural activity signal records and generate the set of stimulation parameters. The user compute device can be further configured to connect to a network and transmit the neural activity signal records, the patient log data, and/or the stimulation parameters to the biobank server. The clinician programmer establishes a second wireless connection to the IPG based on the activation of the first wireless connection, receives the neural activity signal records, and set the stimulation parameters based on the neural activity signal records.

As shown in FIG. 2B, a deep brain stimulation system may include an IPG, a personal controller, and a clinician programmer. The IPG may acquire and store neural activity signal records of a patient and apply electrical stimulations to the patient. The personal controller establishes a wireless connection to the IPG, receive the neural activity signal records, and recharge a battery of the IPG. The personal controller may operatively couple (e.g., a Bluetooth connection, a WiFi connection, and/or the like) to and transmits the neural activity signal records and/or the patient log data to the clinician programmer device. The clinician programmer device may analyze the neural activity signal records and/or the patient log data to determine the medication-on time intervals and the medication-off time intervals based on the neural activity signal records and generate the set of stimulation parameters. The clinician programmer device may connect to a network and transmit the neural activity signal records, the patient log data, and/or the stimulation parameters to the biobank server.

Figure 3A:
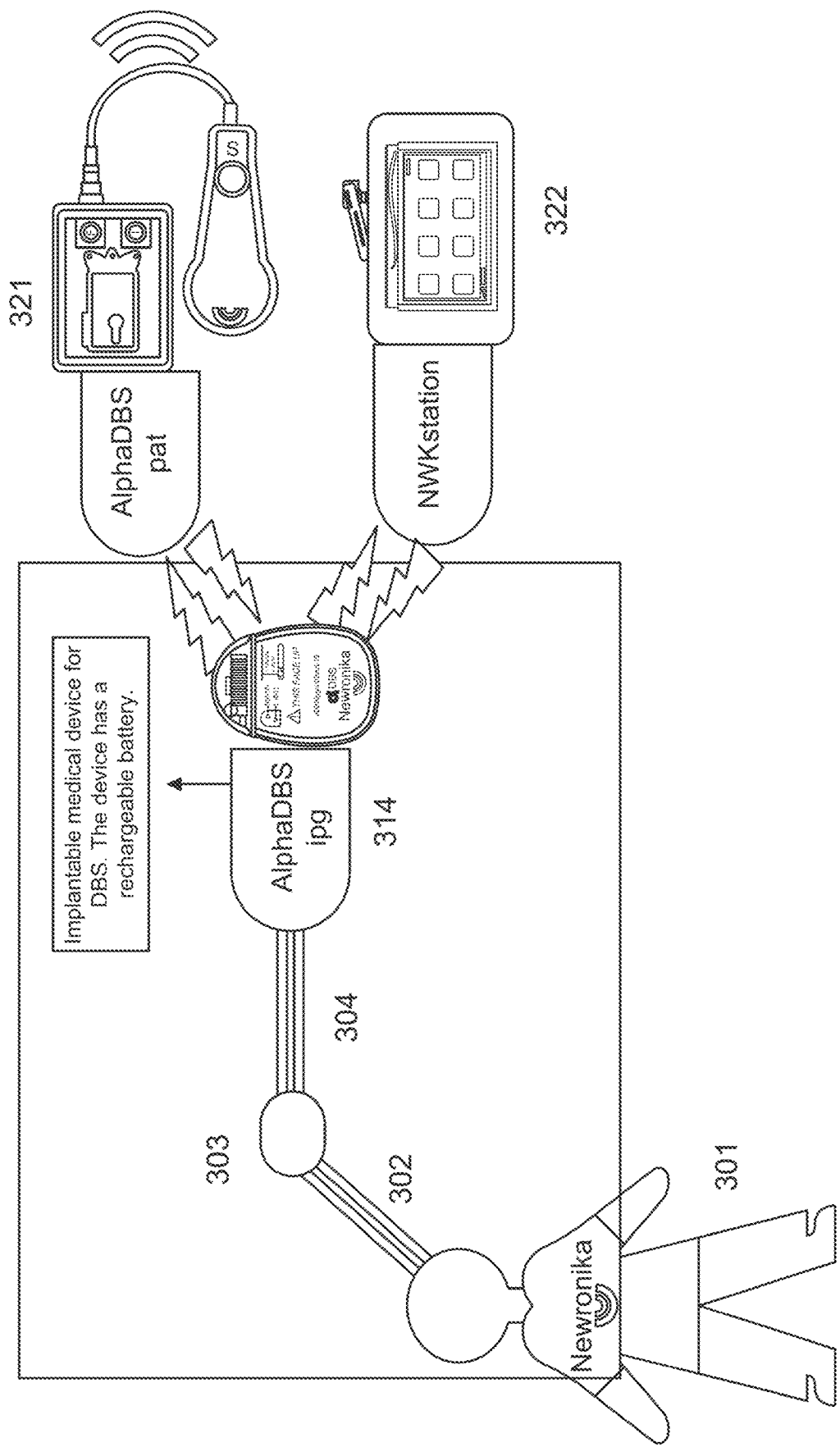
FIG. 3A is a schematic description of an exemplary clinician programmer device.

FIG. 3A is a schematic description of one variation of a deep brain stimulation system. The deep brain stimulation system may include an IPG 314, a patient controller device 321, and a clinician programmer device 322. The IPG 314 can be operatively connected to a patient 301 via an implantable probe(s) 302, a Burr hole cap(s) 303, and a probe extension(s) 304 to record neural activity signals and provide stimulations to the patient 301. The IPG 314 can record and store neural activity signal of the patient 301 and operatively couple to the patient controller device 321 and the clinician programmer device 322. In some instances, the patient may be wearing a T-shirt that helps aligning the patient controller device 321 with the IPG 314 for data communication and power induction. The patient controller device 321 may store the neural activity signal records from and provide power to the IPG 314. In some instances, the neural activity signal records are removed from a memory of the IPG once transmitted to the patient controller device 321. The clinician programmer 322 may also receive the neural activity signal records from the IPG 314 and set the stimulation parameters to the IPG 314 based on the neural activity signal records.

Figure 3B:
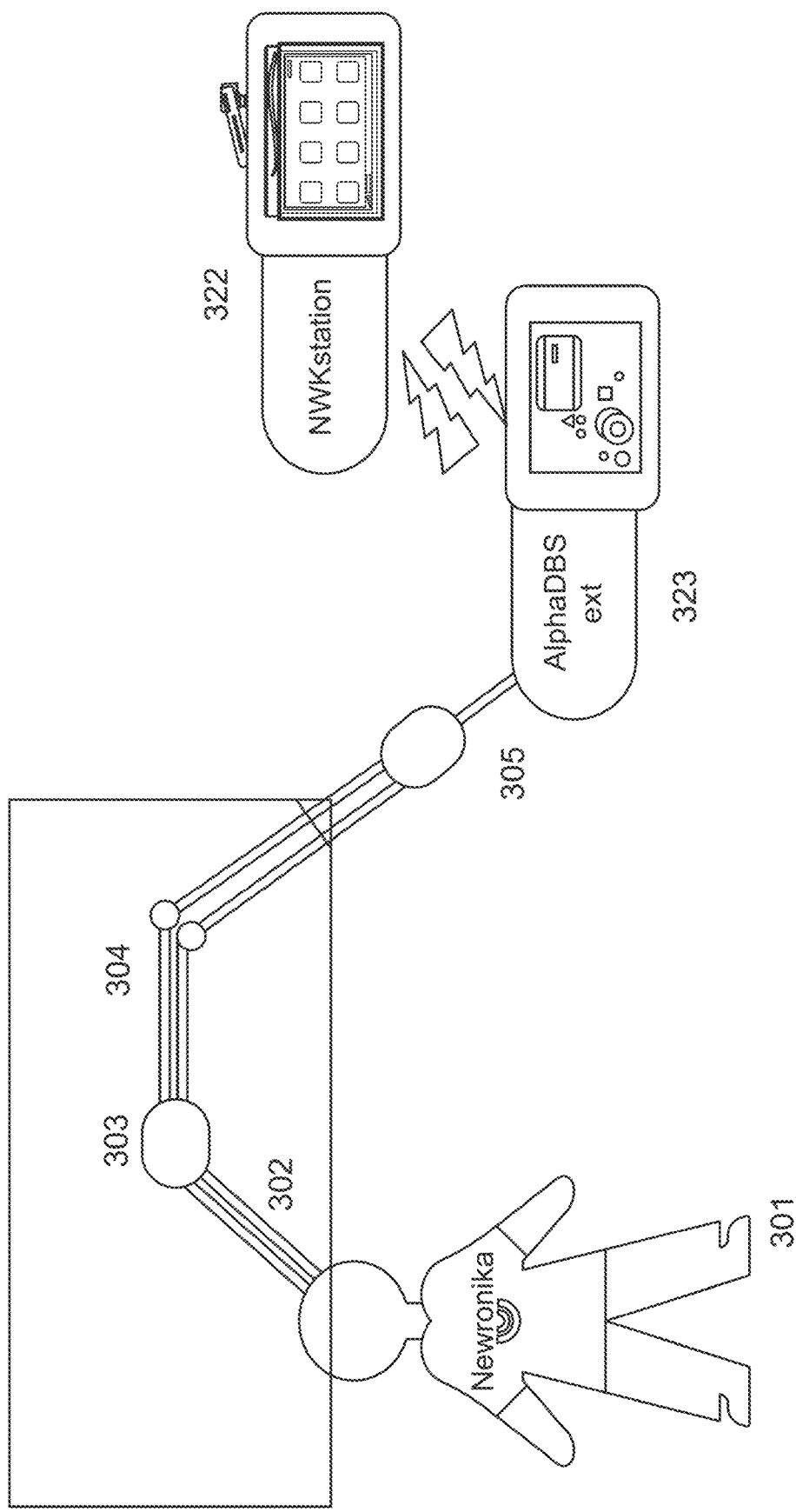
FIG. 3B is a schematic description of an exemplary implantation of an implantable device.

FIG. 3B is a schematic description of one variation of a deep brain stimulation system that may be used to implant one or more probes in a patient. The deep brain stimulation system may be used by a clinician for an open stimulation session (e.g., in a hospital, a physician office, and/or the like). During the open stimulation session, the deep brain stimulation system may be configured to include a clinician external device 323 that is connected, via a probe adapter 305, to the probe extension 304. The clinician external device 323 can generate a set of stimulations to be transmitted to the patient 301 and store neural activity signal records to a memory (not shown) of the clinician external device 323. The clinician external device 323 may operatively couple and transmit the neural activity signal records to the clinician programmer device 322.

Figure 4A:
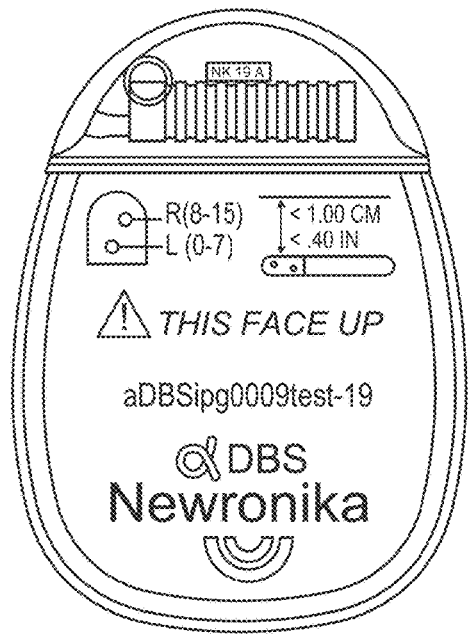
FIG. 4A is a schematic depiction of one variation of an external housing of an implantable device.
Figure 4B:
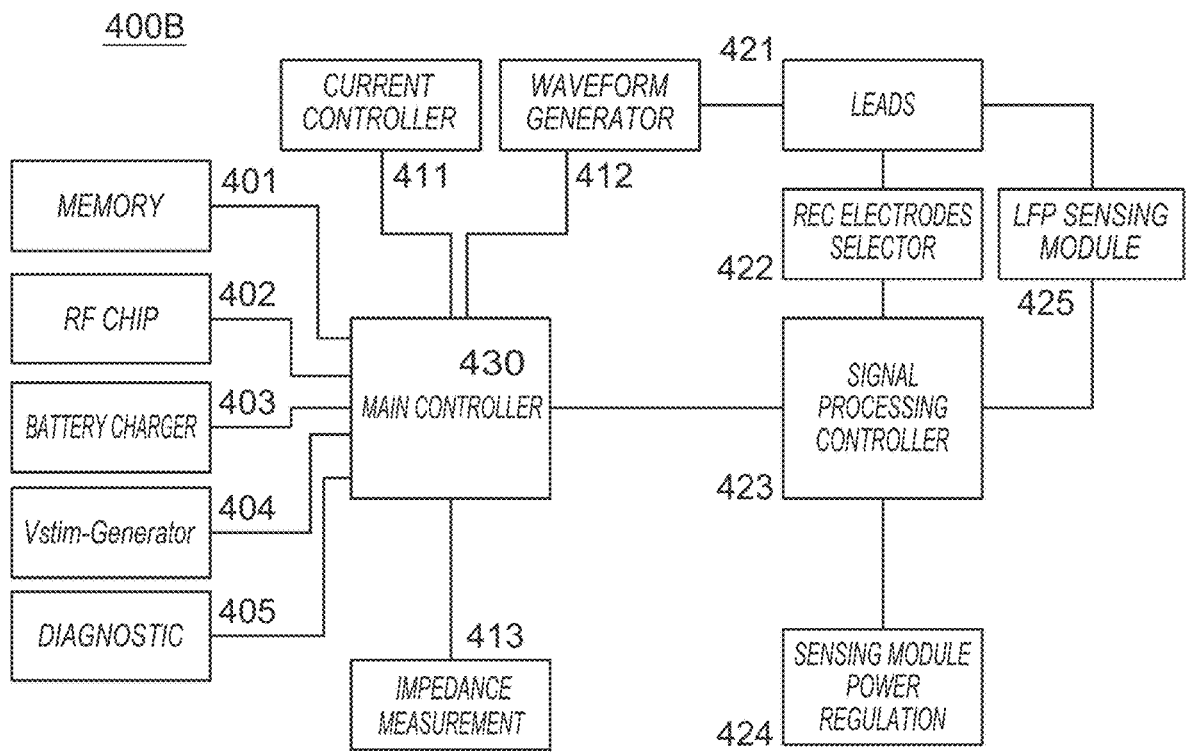
FIG. 4B is a block diagram of an exemplary implantable device.

FIG. 4A is a schematic depiction of one variation of an external housing of an implantable device. Since the implantable device (also referred to herein as the 'implantable pulse generator (IPG) device') may be implanted in a patient it may be compact and have a small volume (e.g., 10 cc, 20 cc, 30 cc, and/or the like) and/or weight (20 grams, 30 grams, and/or the like). FIG. 4B is a block diagram of one variation of an implantable device. The implantable device 400B includes a memory 401, an RF chip 402, a battery charger 403, a $V_{stim}$-generator 404, and a main controller 430. The implantable device 400B may further include a diagnostic device 405, a current controller 411, a waveform generator 412, an impedance measurement device 413, a probe 421, a REC electrode selector, a signal processing controller 423, a sensing device power regulator 424, and a local filed potential (LFP) sensing device 425.

The memory 401 may store data including the set of neural activity records, the set of stimulation parameters, and/or the like. The RF chip 402 may process incoming electromagnetic waves and/or process a set of electrical signals received from the main controller 430 to generate outgoing electromagnetic waves. The battery charger 403 may include a set of electrical circuitry to provide power and charge a battery of the implantable device 400B. The $V_{stim}$-generator 404 may generate stimulation voltage dynamic. The main controller 430 may include, for example, a hardware based integrated circuit (IC) or any other suitable processing device configured to run or execute a set of instructions/codes. For example, the main controller 430 can include a general purpose processor, a central processing unit (CPU), an application specific integrated circuit (ASIC), a microcontroller, and/or the like. The main controller 430 may operatively couple to and transmit a set of instruction (e.g., via set of electrical circuitry) to the memory 401, the RF chip 402, the battery charger 403, the Vstim-generator 404, the diagnostic device 405, the current controller 411, the waveform generator 412, the impedance measurement device 413, the probe 421, the REC electrode selectors, the signal processing controller 423, the sensing device power regulator 424, the LFP sensing device 425.

In some implementations, the implantable device 400B can be initialized by a patient personal controller device. The patient personal controller device can operatively couple to the implantable device 400B to set an initial set of parameters (e.g., a set of cDBS parameters for initial treatment and/or neural activity signal record data collection) to initiate the implantable device 400B. In some implementations, the implantable device can be programmed by a clinician programmer device. The clinician programmer device can operatively couple to the implantable device 400B to program the implantable device 400B with a set of stimulation parameters (e.g., a set of aDBS parameters for a patient-specific and adaptive treatment and/or neural activity signal record data collection).

Figure 5:
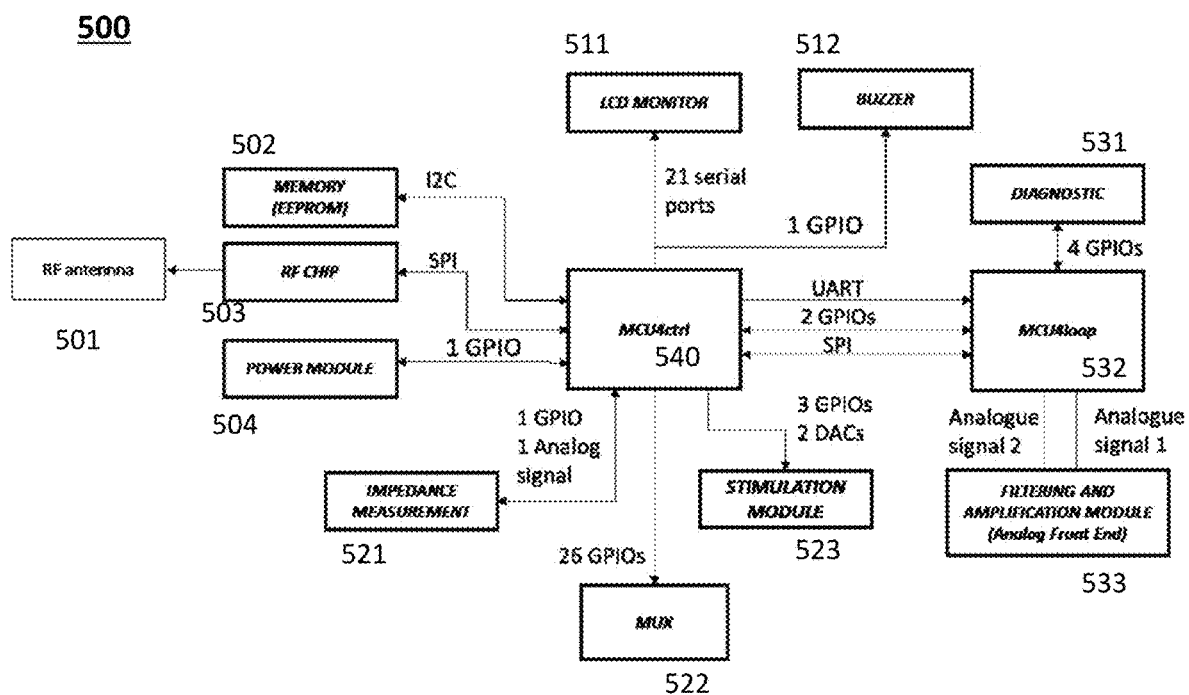
FIG. 5 is a block diagram of an exemplary clinician external device.

FIG. 5 is a block diagram of an exemplary clinician external device 500, according to some variations. The clinician external device 500 (such as the clinician external device as shown and describe with respect to FIG. 3B) is an external device for impedance measurement in the operating room from externalized probe extensions and may be used by a clinician (e.g. a physician, a nurse, etc.) on a day of implantation to confirm electrodes are properly placed. The clinician external device 500 may include an RF antenna 501, a memory 502, an RF chip 503, a power device 504, a display 511 (e.g., LCD monitor), a buzzer 512, an impedance measurement portion 521, a multiplexer 522, a stimulation device 523, a diagnostic device 531, a filtering and amplification device 533, and a control device 540.

Figure 6A:
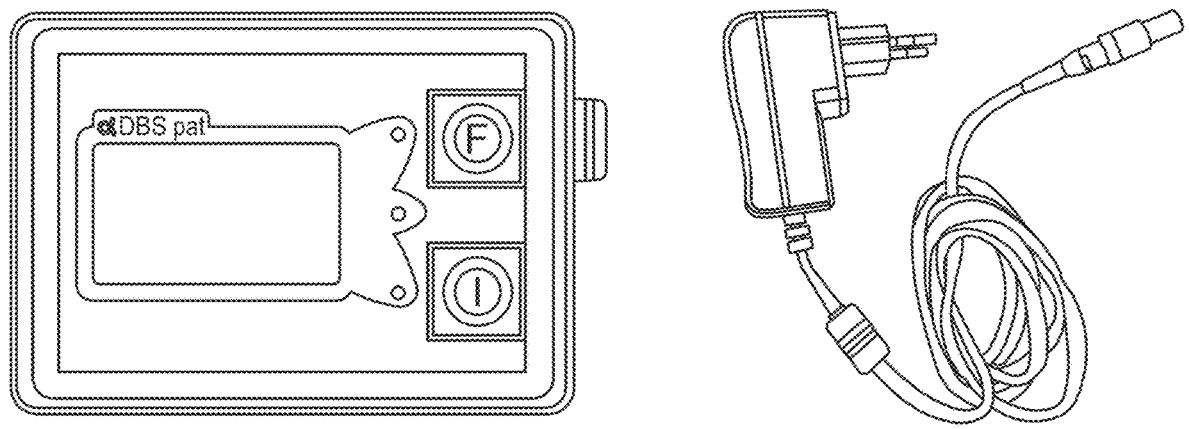
FIGS. 6A and 6B are schematic descriptions of an exemplary patient personal controller device.
Figure 6B:
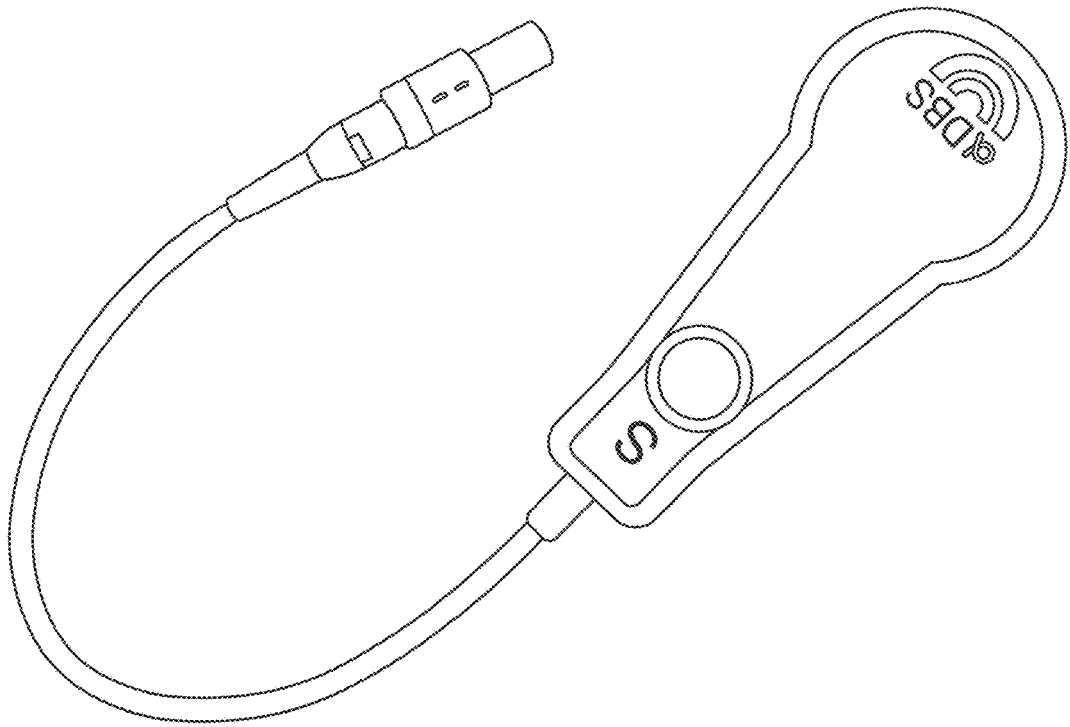

FIGS. 6A and 6B are schematic depictions of subcomponents of an exemplary patient personal controller device. The patient personal controller device (such as the patient controller device 111 as shown and describe with respect to FIG. 1) may include two subcomponents: a recharger unit (FIG. 6B) for recharging the implantable device and a power bank (FIG. 6A) that can connect to and provide power to the recharger unit through a cable. In some implementation, each of the recharger unit and the power bank may include a processor, a memory, and a communication interface structurally and/or functionally similar to the processor 102, the memory 103, and the communication interface 104, respectively, as shown and described with respect to FIG. 1. The recharger unit may receive a set of neural activity signal records from the implantable device over a communication channel between the two and store the receive set of neural activity signal records in the memory of the recharger unit. The recharger unit may transmit the set of neural activity neural activity signal records in the memory of the power bank.

The recharger unit may establish the communication channel (e.g., via a radio frequency (RF) communication channel) with the implantable device to switch the implantable device on or off and/or check a remaining battery level of the implantable device. The power bank may include a user interface that include a graphical user interface (GUI) to display information to a user of the patient personal controller device and/or a set of buttons to receive commands from the user. A status update of remaining charge (remaining battery level) on the implantable device, the recharge unit, and/or the power bank can be displayed on the GUI of the power bank. Moreover, status updates of the treatment status and notifications of any malfunctions can be displayed on the GUI. In some instances, the power bank and/or the recharger unit can generate warning sign for notifying malfunctions and/or low battery levels. In some instances, the recharger unit may be used to initialize/activate the implantable device. Initialization/activation may involve setting an initial set of stimulation parameters and/or charging power of the implantable device. Similarly, the recharger unit may be used to de-activate/shut-off the implantable device.

Figure 7:
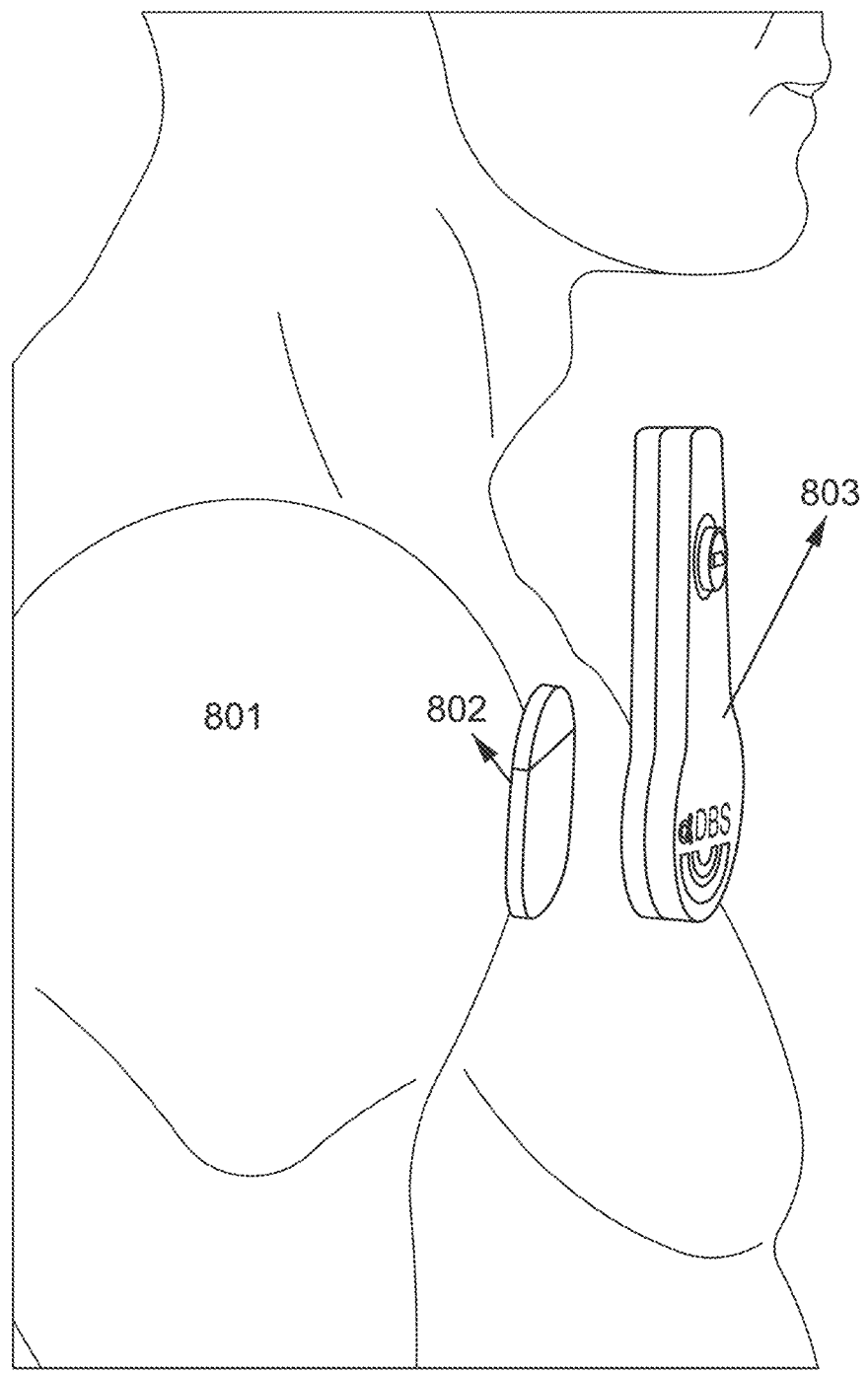
FIG. 7 is schematic depiction of an exemplary method for establishing a wireless connection between an implantable device and a patient personal controller device.

FIG. 7 is a schematic depiction of an exemplary method for establishing a wireless connection between an implantable device (also referred to herein as the 'implantable pulse generator (IPG) device') and a patient personal controller device. The patient personal controller device may transmit power over the wireless connection to charge the IPG. Alternatively, or additionally, the IPG device may transmit/receive neural activity signal records and/or stimulation parameters to/from the patient personal controller device. For example, the IPG may transmit neural activity signal records over the wireless connection to the patient personal controller device, and the personal controller device may transmit stimulation parameters or instructions over the wireless connection to the IPG. In some instances the wireless connection between the implantable device and the patient personal controller device (e.g., a recharger unit of the patient personal controller device) may be established when the patient personal controller device and the implantable device are at a predetermined distance range (e.g., 2 centimeter to 10 centimeter, 1 millimeter to 1 meter, and/or the like) and orientation range. The orientation range can involve, for example, alignment of a vertical orientation of the patient personal controller device to a vertical orientation of the implantable device within 5 rotation degree error margin, 10 rotation degree error margin, and/or the like.

Figure 8:
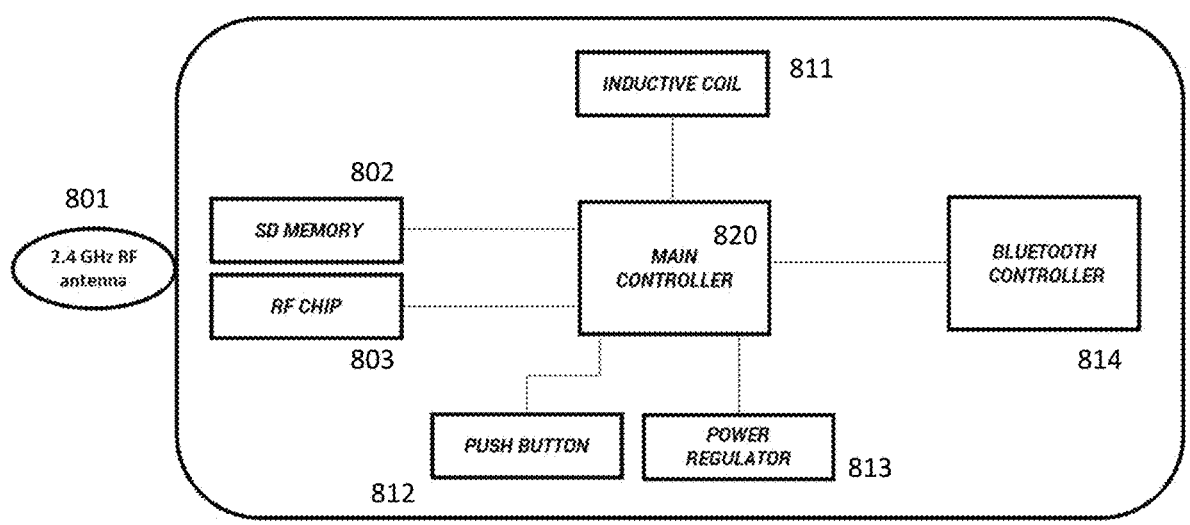
FIG. 8 is a block diagram of an exemplary patient personal controller device.

FIG. 8 is a block diagram of one variation of a patient personal controller device 800 (such as the patient personal controller device as shown and described with respect to FIG. 1). The patient personal controller device 800 may be used by a patient to charge the implantable device and/or download neural activity signal data recorded by the implantable device (as shown and described with respect to FIG. 6 and FIG. 7). The patient personal controller device 800 includes an antenna 801 (e.g., a 2.4 GHz RF antenna), a memory 802 (e.g., a secure digital (SD) card memory), an RF chip 803, an inductive coil 811, a push button 812, a power regulator 813, a main controller 820, and a Bluetooth controller 814.

The antenna may transmit and receive incoming electromagnetic waves representing data that may include a set of neural activity records, a set of stimulation parameters, and/or the like. The RF chip 803 may process the incoming electromagnetic waves received by the antenna and/or process a set of electrical signals received from the main controller 820 to generate outgoing electromagnetic waves. The memory 802 may store data including the set of neural activity records, the set of stimulation parameters, and/or the like. The inductive coil 811 may generate magnetic flux to induce power to an implantable device (not shown). The push button 812 may be activated by a user of the patient personal controller device 800 to initiate, activate/deactivate, and/or establish a communication with the implantable device. The power regulator 813 may include a set of electrical and/or electronic circuitry to regulate characteristic of power induced to the implantable device via the inductive coil 811. The Bluetooth controller 814 may include a set of electrical, electronic, and/or RF circuitry to process and/or generate a set of Bluetooth signals. The main controller 820 may include, for example, a hardware based integrated circuit (IC) or any other suitable processing device configured to run or execute a set of instructions/codes. For example, the main controller 820 can include a general purpose processor, a central processing unit (CPU), an application specific integrated circuit (ASIC), a microcontroller, and/or the like. The main controller 820 may operatively couple to and generate a set of instructions to the memory 802, the RF chip 803, the inductive coil 811, the push button 812, the power regulator 813, and/or the Bluetooth controller 814.

Figure 9A:
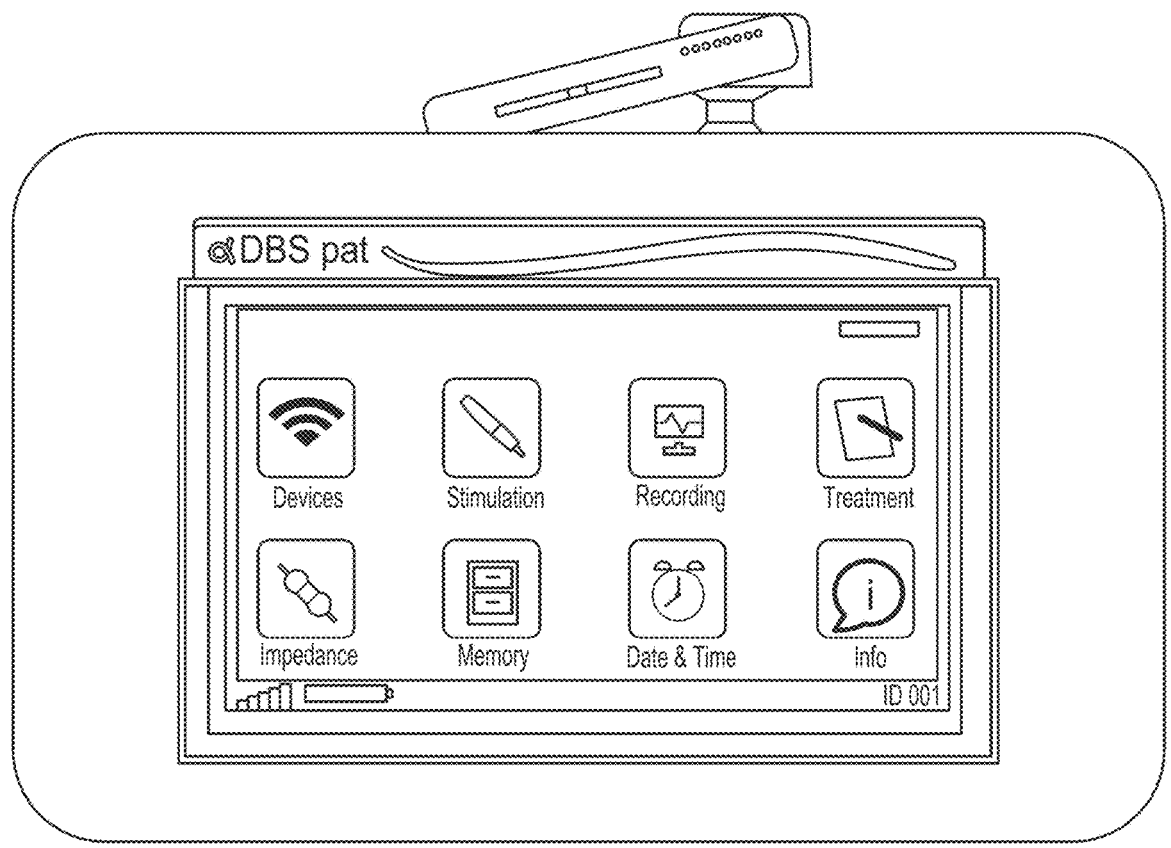
FIGS. 9A and 9B are schematic descriptions of an exemplary clinician programmer device.
Figure 9B:
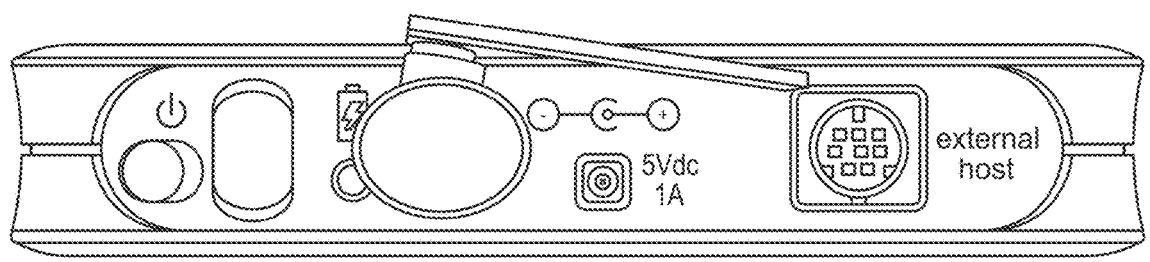

FIGS. 9A and 9B are schematic descriptions of an exemplary clinician programmer device (such as the clinician programmer device 131 as shown and described with respect to FIG. 1). As shown in FIG. 9A, the clinician programmer device may include a graphical user interface (GUI). In some instances, the GUI may be a touch screen panel such that a user of the clinician programmer device (e.g., a clinician, a physician, a nurse, and/or the like) may interact with the clinician programmer device via the GUI.

The clinician programmer device may include/implement a variety of software applications including, a connection application to check status of connectivity with other device, a stimulation application to provide stimulation to a patient, and/or a recording application to record neural activity records received from an implantable device and/or a patient personal controller device. The clinician programmer device may further include/implement a treatment application to set a treatment mode by the user of the clinician programmer device, an impedance application to measure and set a set of impedances of electrodes operatively coupled to the clinician programmer device, and/or other suitable applications for the clinician programmer device (e.g., patient information card application, operating system version info, date/time applications, memory application, processor application, etc.).

As shown in FIG. 9B, the clinician programmer device may include a panel interface (e.g., a back panel interface, a top panel interface, and/or the like). In some instances, the panel interface may include a power button to turn the clinician programmer device on/off and/or an antenna to receive and/or transmit electromagnetic waves representing data from/to the implantable device, the patient personal controller device, a network (e.g., Internet) and/or the like. The panel interface may further include a power plug port to receive power from an alternating current (AC) and/or direct current (DC) power source and charge a battery of the clinician programmer device. The panel interface may provide a universal serial bus (USB) type port for connection to external hosts.

Figure 10:
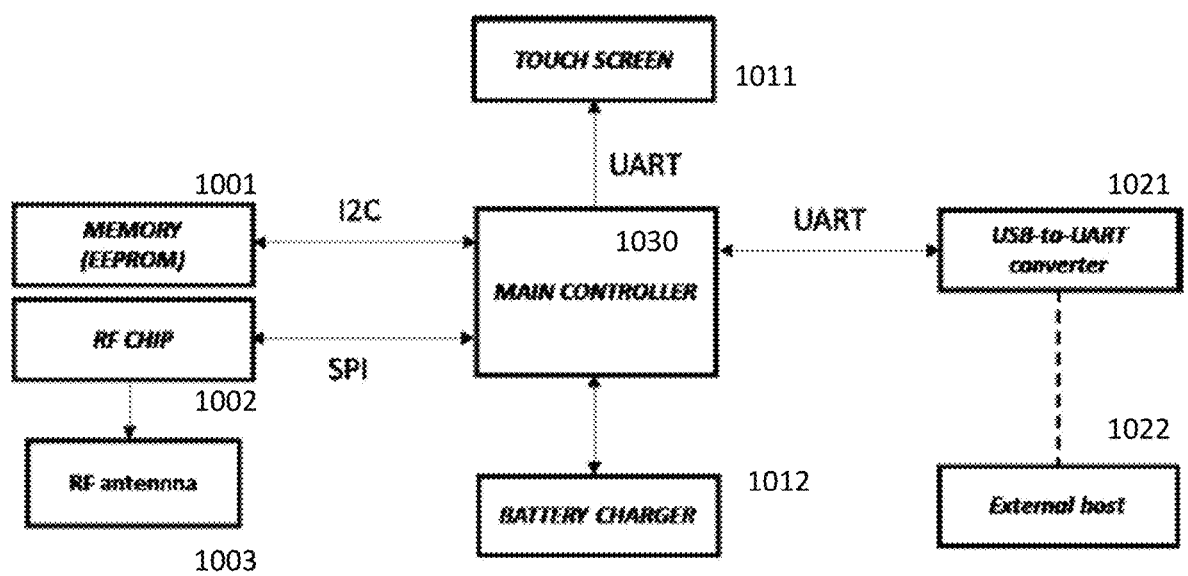
FIG. 10 is a block diagram of an exemplary clinician programmer device.

FIG. 10 is a block diagram of an exemplary clinician programmer device 1000. The clinician programmer device 1000 includes a memory 1001 (e.g., an electrically erasable programmable read-only memory (EEPROM) memory), an RF chip 1002, an antenna 1003 (e.g., an RF antenna), a touch screen 1011, a battery charger 1012, a main controller 1030, and a USB-to-UART converter 1021, and may connect to an external host 1022.

The antenna 1003 may transmit and receive incoming electromagnetic waves representing data that may include a set of neural activity records, a set of stimulation parameters, and/or the like. The RF chip 1002 may process the incoming electromagnetic waves received by the antenna and/or process a set of electrical signals receive from the main controller 1030 to generate outgoing electromagnetic waves. The memory 1001 may store data including the set of neural activity records, the set of stimulation parameters, and/or the like. The battery charger 1012 may include a set of electrical circuitry to provide power and charge a battery of the clinician programmer device 1000. The touch screen 1011 may display a set of images to the user of the clinician programmer device 1000 and receive a set of commands from the user by touching the touch screen 1011. The USB-to-UART converter 1021 may convert universal asynchronous receiver-transmitter (UART) port communication to universal serial bus (USB) port communication for interfacing with external hosts 1022 (e.g., a laptop computer, a desktop computer, and/or the like). The main controller 1030 may include, for example, a hardware based integrated circuit (IC) or any other suitable processing device configured to run or execute a set of instructions/codes. For example, the main controller 1030 can include a general purpose processor, a central processing unit (CPU), an application specific integrated circuit (ASIC), a microcontroller, and/or the like. The main controller 1030 may operatively couple to and generate a set of instruction to the memory 1001, the RF chip 1002, the antenna 1003, the touch screen 1011, the battery charger 1012, the main controller 1030, the USB-to-UART converter 1021, and/or the external host 1022.

Methods for Adaptive Deep Brain Stimulation (aDBS) Programming

Described herein are an implantable device (also referred to herein as the 'implantable pulse generator (IPG) device') that may provide adaptive deep brain stimulation (aDBS) and/or conventional deep brain stimulation (cDBS). An aDBS mode may change a set of stimulation parameters in real-time based on a set of control variables and the patient's neural activity. More specifically, in aDBS mode, the IPG device records the neural activity signals (e.g., local field potentials (LFPs)) from one or more electrodes of a deep brain stimulation (DBS) probe. The IPG device can then store the neural activity signals records as sample/digitized representations of the neural activity. The IPG device may be further configured to extract the neural activity signal records in a specific frequency band (e.g., alpha band, beta band, 12 Hz to 35 Hz, and/or the like) and adapts the set of stimulation parameters (e.g., stimulation amplitude, stimulation pulse width, and/or the like) based on a linear relationship. The power of beta oscillations may linearly correlate with a patient's clinical state. In other terms, neural activity signal records with higher beta power values may imply worse clinical states and may therefore need higher stimulation amplitudes. Such a linear relationship, when quantitatively implemented in the IPG device may require, however, to be calibrated in a patient-specific fashion. Thus, a patient-specific symptom control deep brain stimulation device can be beneficial.

When the aDBS mode is activated on the IPG device, the amplitude of a deep brain stimulation (DBS) is automatically determined/set by a deep brain stimulation system (such as the deep brain stimulation system 100 as shown and described with respect to FIG. 1) according to the neural activity signals recorded by the DBS electrodes. More specifically, the aDBS mode modifies the stimulation amplitude following the power of the local field potentials (LFP) oscillation in a specific band such as, for example, the beta band (10-35 Hz). A specific patient may have a different central frequency in the beta band and a different beta power value. Also, the specific patient may have a different response to DBS and requires a specific stimulation intensity to control the patient-specific symptoms of the specific patient. Therefore, to setup aDBS mode correctly, a treating clinician may define a set of parameters including:

$P_{\beta MIN}$: an average minimum power (also referred to herein as a first average value) reached by the beta band oscillation in the specific patient (this is usually associated with the ON medication condition)

$P_{\beta MAX}$: an average maximum power (also referred to herein as a second average value) reached by the beta band oscillation in the specific patient (this is usually associated with the OFF medication condition)

$A_{min}$: a minimum DBS amplitude eliciting a detectable clinical effect in the specific patient $A_{max}$: a maximum DBS amplitude before eliciting a side effect in the specific patient.

$V_{DBS}$: the DBS amplitude output.

The set of parameters allows to calibrate the aDBS mode:

$$V_{DBS} = \frac{P_\beta - P_{\beta MIN}}{P_{\beta MAX} - P_{\beta MIN}} * (A_{MAX} - A_{MIN}) + A_{MIN}$$

where $P_\beta$ is a power (or amplitude) of the neural activity signals in the beta frequency band that may be measured by the electrodes on the implanted probes.

FIG. 11 is a method 1100 for selecting a set of sensing electrodes, a set of stimulation electrodes, and power bands. The method 1100 comprises, at 1101, checking impedance of a set of electrode pairs and excluding a subset of electrode pairs from the set of electrode pairs that have aberrant impedance values. The method 1100 further comprises, at 1102, screening power spectrum of a set of neural activates (e.g., local field potential (LFP) activities) on the remaining electrode pairs. The method 1100 further comprises, at 1103, titrating a therapeutic window and defining a $A_{max}$ and $A_{min}$. $A_{max}$ and $A_{min}$ may be measured when the patient is not taking medication. The method 1100 further comprises, at 1104, selecting electrode pairs for sensing and showing a highest beta activity excluding the stimulation electrodes. In some instances, $A_{max}$ and $A_{min}$ may be determined when the patient is on medication.

In some implementations, the method 1100 may be implemented using a clinician programmer device (such as the programmer device 131 as shown and described with respect to FIG. 1) and/or using a user compute device (such as the user compute device 121 as shown and described with respect to FIG. 1). The clinician programmer device can be configured to check impedances of all electrode pairs available. Alternatively or additionally, electrode impedance checks may also be performed using clinician external device at the time the probe is implanted. Each electrode with an impedance out of an allowed impedance range such as, for example, an allowed impedance range of 500-2000 Ohms, are stored in a memory of the clinician programmer device (stored in the memory 133 of the programmer device 131 as shown and escribed with respect to FIG. 1). Such electrodes with an impedance out of the allowed impedance range are excluded for stimulation and/or recording. The clinician programmer device performs a short term (e.g., 10-30 seconds, and/or the like) recording of a set of neural activities (e.g., an LFP activities) for each electrode pair available (excluding the ones with aberrant impedances values) when a patient is in a off-medication state. To ensure a proper recording condition, it is recommended to perform the short term recording of the set of neural activities when the patient is in the off-medication state, in which Parkinson's symptoms are predominant (e.g., after an overnight stimulation and a pharmacological withdrawal). The clinician programmer device can be configured to review the characteristics of the short term recording of the set of neural activities in the therapeutic window (e.g., a predefined frequency domain). The therapeutic window generally shows an oscillatory activity that characterizes the short term recording of the set of neural activities. In some instance, the oscillatory activity is identified by a peak in the therapeutic window of the short term recording of the set of neural activities. The peak may be characterized by an intensity (also referred to herein as "spectral power") and may be reported/displayed in the clinician programmer device. The clinician programmer device further stores a peak frequency (i.e., a frequency at which the power spectrum has the highest value) and the power spectrum associated with the short term recording of the set of neural activities. The clinician programmer device performs the above mentioned procedure for each electrode pair available (bilaterally).

The clinician programmer device can be configured to select a set of electrodes on one or more implanted probes that allow a best patient-specific symptom control with a lowest side effects (i.e., clinical outcomes) and lower energy delivered to a tissue of the patient. Each electrode may include a broadband spectral property and may record neural activity signals with a broad spectral range. The clinician programmer device may use the selected electrodes even if the selected electrodes have been already identified for the short term recording of the set of neural activities. The clinician programmer device may further define $A_{min}$ (minimum amplitude eliciting a clinical benefit for the patient) and $A_{max}$ (maximum amplitude before eliciting side effects) related to the selected electrodes. The clinician programmer device may store $A_{min}$ and/or $A_{max}$ in the memory of the clinician programmer device. The clinician programmer device can be further configured to identify an electrode pair with the strongest beta frequency band component (excluding the electrode pairs chosen for stimulation and the electrodes with aberrant impedances) with the highest power in the beta frequency band (e.g., between 10 Hz and 35 Hz). Although the beta frequency band is generally understood to in range of ~10-30 Hz, a patient-specific beta frequency band may vary among patients and may be determined by the deep brain stimulation system in order to personalize the aDBS mode for the patient. This is because for each patient a peak of power (also referred to as 'patient-specific power') of neural activity signals of may occur at a different frequency. For example, patient A may have more activity at 15 Hz than at 25 Hz, while Patient B may have a peak of activity at 20 Hz with much lower activity in other frequencies in the beta band, and while Patient C may have more activity at 30 Hz than at 10 Hz, etc. The clinician programmer device can be configured to determine and/or select a range/boundaries (+/−2 Hz, +/−3 Hz, etc.) for a patient-specific frequency band. For example, the patient-specific beta frequency band can be +/−2 Hz around a beta peak measured for the patient.

The implantable pulse generator (IPG) device acquires and/or stores neural activity signal records such as, for example, local field potentials (LFPs) for a predefined time period. The predefined time period can be determined by a clinician and in some variations, may be about 1 week, 2 weeks, 20 weeks, 1 day, 10 days, 15 days, 30 days, 45 days, 60 days, and/or the like. The IPG device acquires neural activity signals over the predefined time period, which may be stored in the memory of the IPG device as neural activity signal records. The IPG and/or any of the external devices described herein (e.g., patient controller device, programmer device, etc.) may calculate the first average value $P_{\beta MIN}$ and the second average value $P_{\beta MAX}$ based on the neural activity signal records from the IPG. The neural activity signal records are recorded from at least one electrode from the electrode pairs selected as described above for sensing and showing a highest beta activity selected. In particular, the IPG device stores, in a non-volatile memory (such as the memory 103 of the implantable device 101 as shown and described with respect to FIG. 1), the spectral features of the neural activity signal records for a set of predefined period. In some instances, a length of each predefined period T can be determined based on a memory space of the memory (e.g., 100 MB, 1 GB, 4 GB, 8 GB, 128 GB, and/or the like). In such instances, a shorter predefined period T is allocated for a larger memory space for better time-resolution of the data. In some instances, in addition to the spectral features of the neural activity signal records, the IPG device can store a patient-specific power from the patient-specific frequency band selected as described above. The value of the patient-specific power from the patient-specific frequency band should be stored at every patient-specific predefined period T'. In some instances, the patient-specific predefined period T' may be set by a physician, determined based on spectral features of the neural activity signal records, and/or predetermined (e.g., based on total and/or remaining data storage capacity, total and/or remaining battery, a trade-off between battery power consumption and time resolution of data, a trade-off between data storage capacity and time resolution of data, and/or the like). For example, the neural activity signal records may on average show a spectral peak or a spectral dip at every time Ti; therefore the patient-specific predefined period T' may be set to a factor (e.g., multiplied by 0.5, 2, 3, etc.) of Tl. In some instances, the patient-specific predefined period T' be equal to the predefined period T. The neural activity signal records are therefore recorded and processed by the IPG for X number of days (e.g., X≥1). The neural activity signal records can be recorded both during deep brain stimulation (DBS) medication-on time intervals (e.g., when a DBS medication is set to on) and/or medication-off time intervals (e.g., when a DBS medication is set to off). The medication-on time intervals and/or the medication-off time intervals can be determined based on a patient-specific medical condition.

In one example, if an IPG device is implanted to replace an old IPG device (e.g., due to a battery depletion of the old IPG device) then a parkinsonian patient can be a patient in an advanced state of a parkinsonian syndrome disease and can potentially not tolerate medication-off time intervals of stimulators of the IPG device. In another example, if an IPG device is implanted for a first time in a patient, then there is usually an adjustment period, in which medication-off time intervals can allow for an adjustment of impedances of electrodes before setting a set of stimulation parameters of a stimulation. The implantation of probes can create a "stunning effect", which includes an edema around the electrodes and can, ultimately, cause a bias in an evaluation of a clinical efficacy of the stimulation. Therefore, it is a common clinical practice to wait for end of the adjustment period to switch on DBS for medication-off time intervals. Such adjustment period is often suitable for collecting data. Preferably the method for collecting data comprises a first number of days X (e.g., X≥1) during which the DBS is switched on so that the neural activity signal records (power spectrum) and/or patient-specific power of the neural activity signal records (e.g., from at least from one electrode) can be acquired and/or stored as data. The data stored in the IPG device can be then downloaded at every cycle of recharge on the patient personal controller device (such as the patient personal controller device 111 as shown and describe with respect to FIG. 1) via, for example, a radio frequency communication channel. The cycles of recharge may be done, for example, once a day, every other day, every 3 days, every 4 days, every 5 days, every week, and/or the like. Once the data is downloaded on the patient personal controller device, the data is deleted from the memory of the IPG device and stored consecutively in a memory (such as the memory 113 as shown and describe with respect to FIG. 1) of the patient personal controller device that can have a larger memory size. In some instances, moving the data from the IPG device to the patient personal controller device allows the IPG device to collect data for a long period of time (e.g., 1 month, 2 months, 3 months, 6 months, 12 months, and/or the like).

Described herein are methods of determining a set of stimulation parameters (can be also referred to herein as 'a set of adaptive rules') to provide an adaptive deep brain stimulation (aDBS) to an implantable pulse generator (IPG) device. The set of stimulation parameters can include the minimum stimulation amplitude $A_{MIN}$, the maximum stimulation amplitude $A_{MAX}$, the first average value represented by $P_{\beta MIN}$, or the second average value represented by $P_{\beta MAX}$. The set of stimulation parameters can collectively define brain stimulation (DBS) amplitudes $V_{DBS}$ by:

$$V_{DBS} = \frac{P_\beta - P_{\beta MIN}}{P_{\beta MAX} - P_{\beta MIN}} * (A_{MAX} - A_{MIN}) + A_{MIN}$$

where $P_\beta$ represents power of a neural activity signal record having a value between the first average value $P_{\beta MIN}$ and the second average value $P_{\beta MAX}$.

In some instances, the minimum stimulation amplitude $A_{MIN}$ and/or the maximum stimulation amplitude $A_{MAX}$ can be determined with regards to a therapeutic window of a specific patient as described above an with respect to FIG. 11. In some instances, the minimum stimulation amplitude $A_{MIN}$ and/or the maximum stimulation amplitude $A_{MAX}$ can be determined empirically by a gradual increase in a stimulation amplitude (e.g., starting from a zero value to a clinician determined stimulation value) and keeping note of clinical outcomes of the gradual increase.

FIG. 12 is an exemplary method 1200 for adaptive deep brain stimulation. The method 1200 can be performed, for example, by a clinician programmer device (such as the clinician programmer device 131 as shown and described with respect to FIG. 1) and/or using a user compute device (such as the user compute device 121 as shown and described with respect to FIG. 1). Method 1200 may comprise extracting 1201 a set of spectral features of a set of neural activity signal records for a predefined number of days, selecting 1202 a set of spectral features within a frequency band of the set of spectral features, selecting 1204 a set of medication-on time intervals and a set of medication-off time intervals during the predefined number of days, generating 1205 a minimum average of the set of selected spectral features within the frequency band and within the set of medication-on time intervals, and generating 1206 a maximum average of the set of selected spectral features within the frequency band and within the set of medication-off time intervals. Optionally, method 1200 may comprise generating 1203 an average of the set of selected spectral features within the frequency band and across the predefined number of days.

Figure 13:
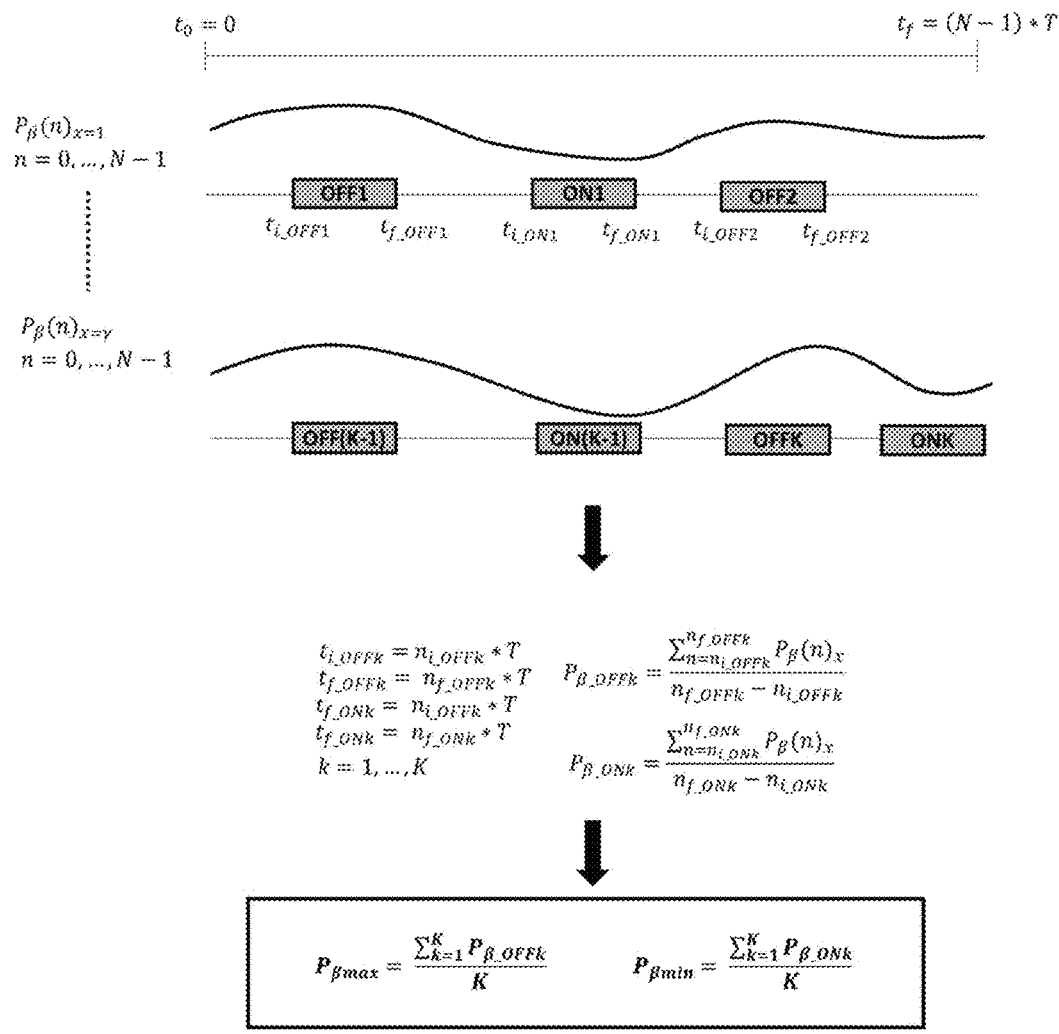
FIGS. 13 and 14 are exemplary methods for programming a clinician programmer device.
Figure 14:
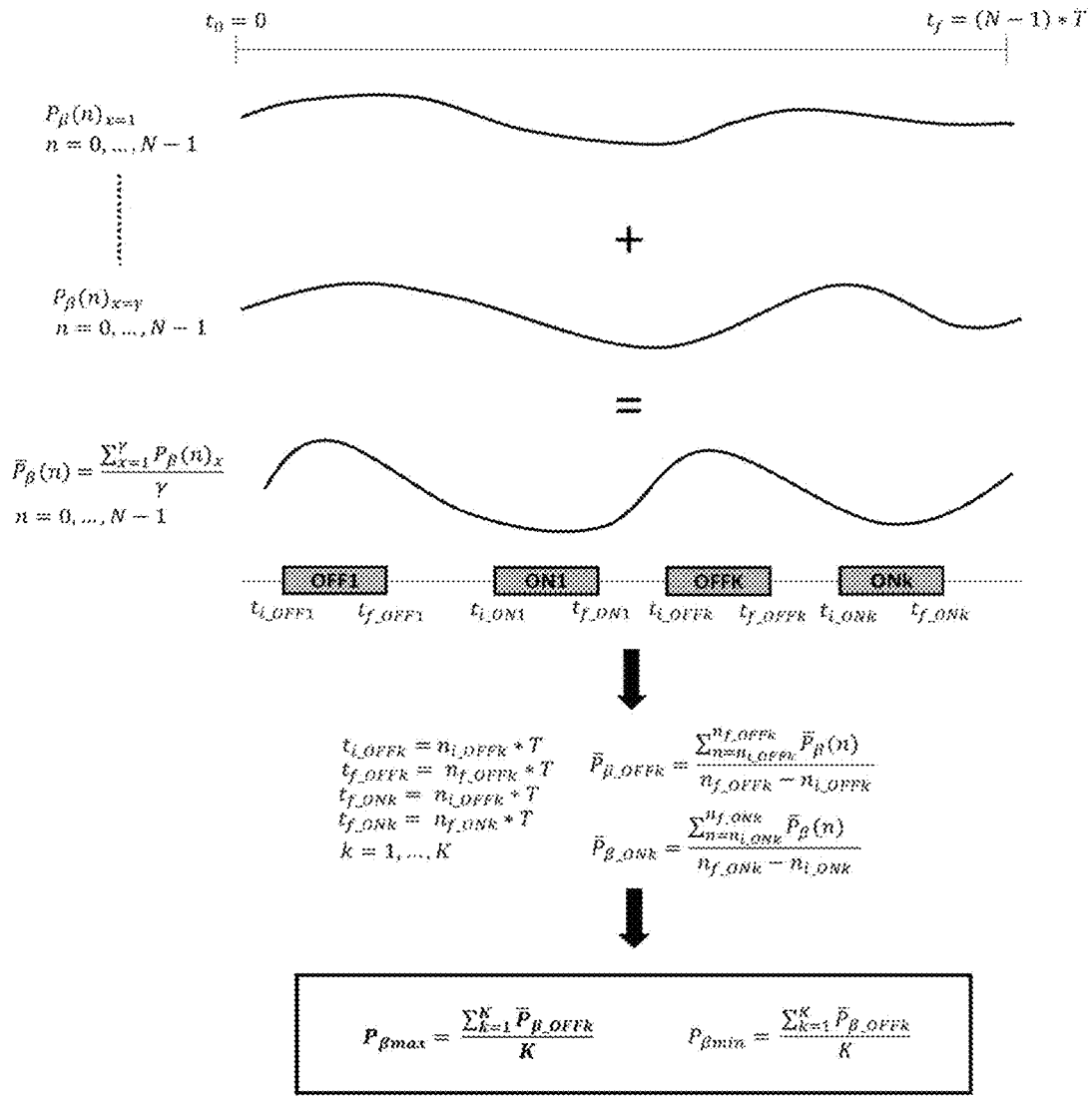

FIGS. 13 and 14 are exemplary method for programming a clinician programmer device for adaptive deep brain stimulation. The method describes obtaining the first average value $P_{\beta MIN}$ and the second average value $P_{\beta MAX}$ as described with respect to FIG. 11. The method involves, collecting local field spectral features for a number of days (e.g., 1 day, 2 days, 10 days, etc.). The method further involves selecting a frequency band for the local field potentials from a low-frequency band, the alpha frequency band, the beta frequency band, or gamma frequencies. The method further involves averaging the power of local field spectral features across the selected frequency band. In some instances, a set of moving average values of the power of local field spectral features across the selected frequency band may be calculated for a set of time period (e.g., 10 minutes, an hour, 6 hours, a day, 2 days, and/or the like). Therefore, a set of medication-on times and medication-off time may be selected among the set of moving average values. In some instances a threshold is determined by a user (e.g., a patient, a clinician, a physician, etc.) and any time periods with moving average value above/below the threshold may be classified as medication-off time/medication-on time. Lastly, the first average value $P_{\beta MIN}$ may be calculated by averaging the power of the selected band across the medication-on times and the second average value $P_{\beta MAX}$ may be calculated by averaging the power of the selected band across the medication-off times.

As describe above, a deep brain stimulation system can store and analyze the set of neural activity signal records to provide stimulation/treatment modes including a conventional deep brain stimulation (cDBS) treatment plan modes and/or an adaptive deep brain stimulation (aDBS) treatment modes. In some instances, a user of a user device (such as the user compute device as shown and described with respect to FIG. 1) may select to use a cDBS treatment mode. The cDBS treatment plan modes may involve setting a set of stimulation parameters including frequency, pulse width and/or amplitude of stimulations. In some instances, the user of the user device may select to use an aDBS treatment mode. The aDBS treatment plan modes may involve setting a set of stimulation parameters including a maximum power, a minimum power, a band length, a minimum stimulation amplitude, a maximum stimulation amplitude, a frequency, a pulse width, and/or the like. Additional variations of stimulation/treatment modes are provided in U.S. Pat. No. 10,596,379, which is hereby incorporated by reference in its entirety.

In some implementations, a user of a clinician programming device and/or a user compute device may select (via a GUI of the clinician programming device) to use an open stimulation mode (also referred to as 'open stimulation session'). During the open stimulation mode, the user may set/assign parameters for probes (e.g., each including a pair of electrodes) to determine stimulation parameters of the open stimulation mode. The parameters may include, for example, stimulation amplitudes of each electrode, frequency, pulse width, and/or the like. In some implementations, the user may select to operate the clinician programming device and/or the user compute device in neural signal recording mode to record neural activity signals (e.g., local field potentials) for a time duration (e.g., 30 seconds) and visualize the power spectrum of the neural activity signal records in a table and/or a graph. In some instances, the graph may include a statistical distribution of the neural activity signal records such as, for example, moving averages, deviations, global average, medium, and/or the like.

Figure 15A:
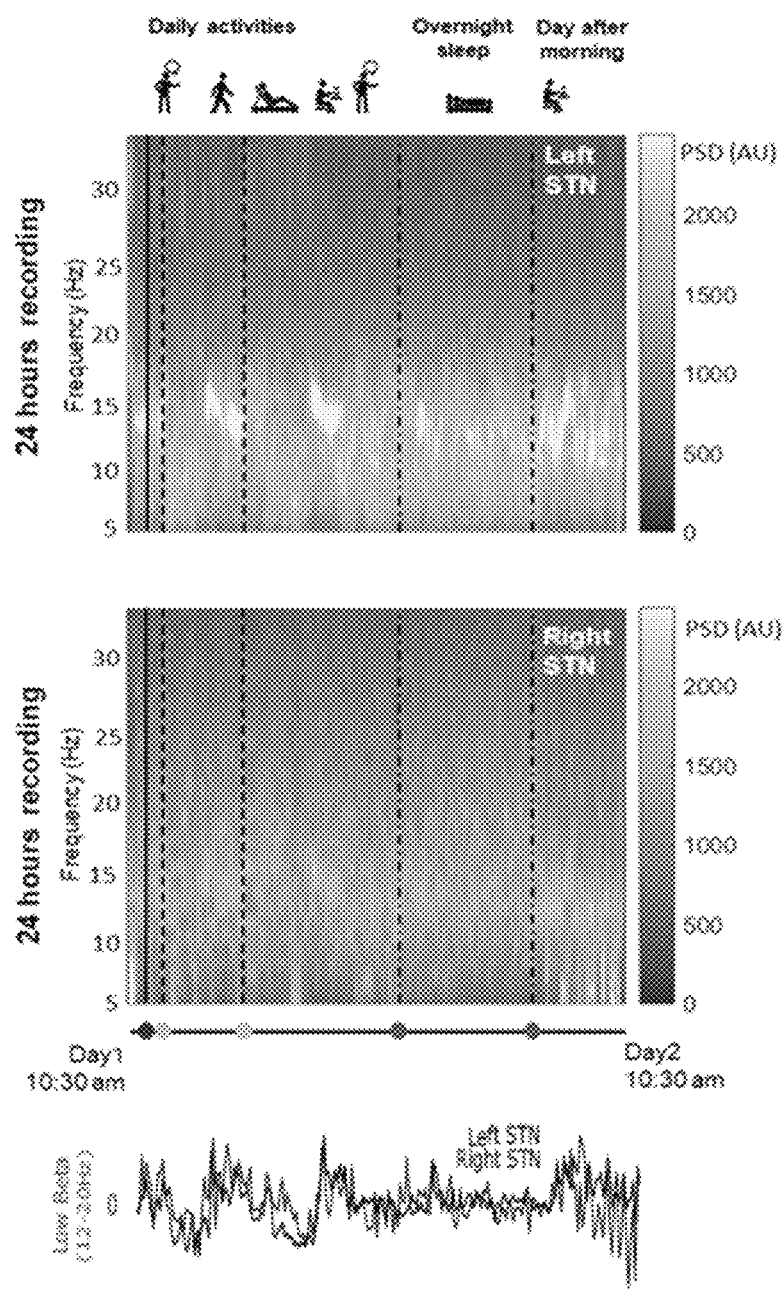
FIGS. 15A and 15B are exemplary neural activity signal records stored an analyzed by a deep brain stimulation system.
Figure 15B:
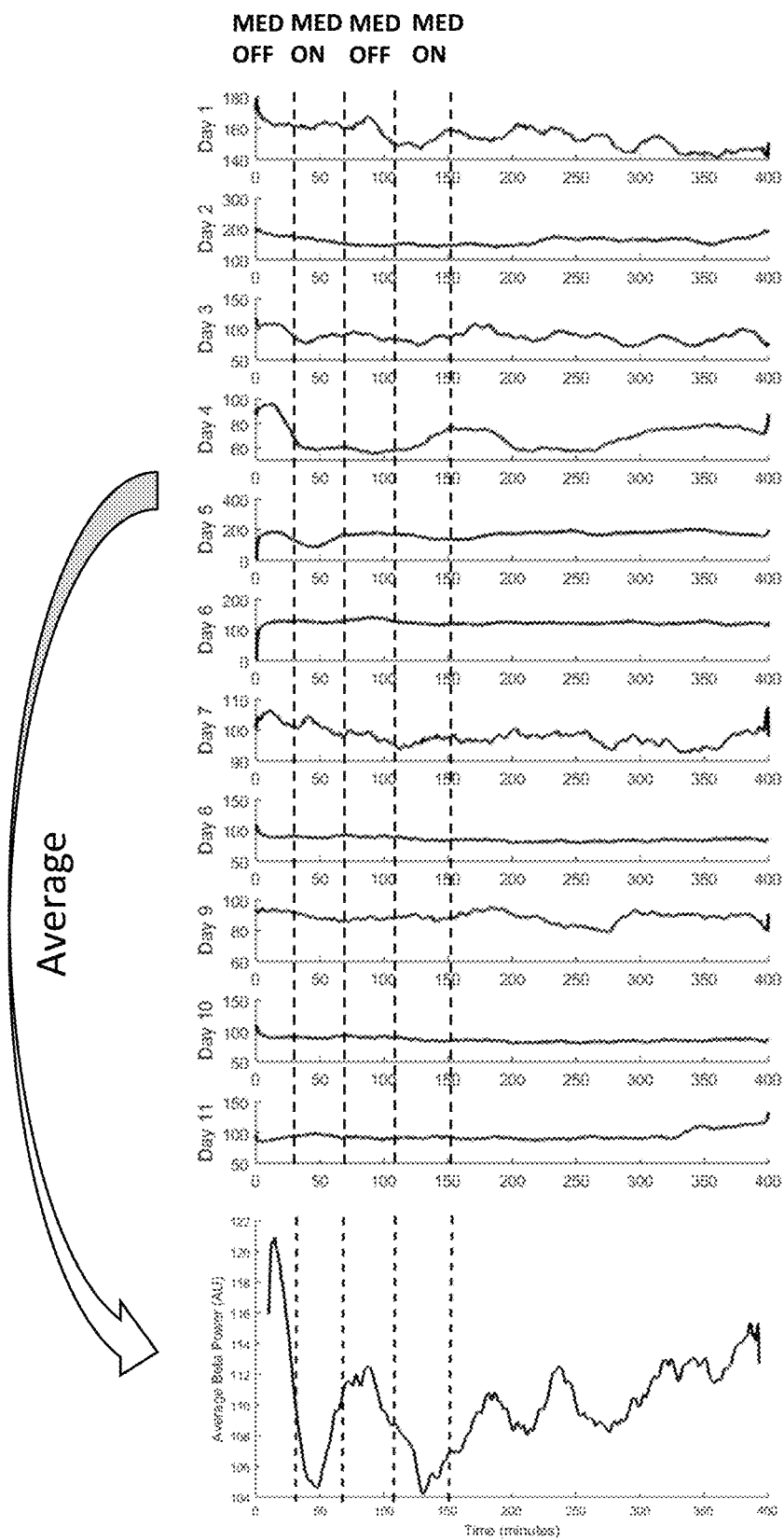

FIGS. 15A and 15B are exemplary neural activity signal records stored an analyzed by a deep brain stimulation system. The deep brain stimulation system, as described above, may acquire and/or store neural activity signal records such as, for example, local field potentials (LFPs) for a predefined time period (e.g., 1 day, 10 days, etc.). For example, as shown in FIG. 15A, in some instances, the neural activity signal records during a day (e.g., during regular daily activities) can be acquired and recorded separately for left subthalamic nucleus (STN) and right STN in a frequency range between 5 Hz to 35 Hz. The deep brain stimulation system can select a frequency band for the neural activity signal record from a low-frequency band, the alpha frequency band, the beta frequency band, and/or gamma frequencies. For example, as shown in FIG. 15A, in some instances, the frequency band between 12 Hz to 20 Hz can be selected for analysis. The deep brain stimulation system can further average the power of the neural activity signal records across the selected frequency band. For example, as shown in FIG. 15B, the averaged neural activity signal records can be further analyzed by the deep brain stimulation system and methods described above to determine medication-on time intervals and medication-off time intervals.

Figure 16:
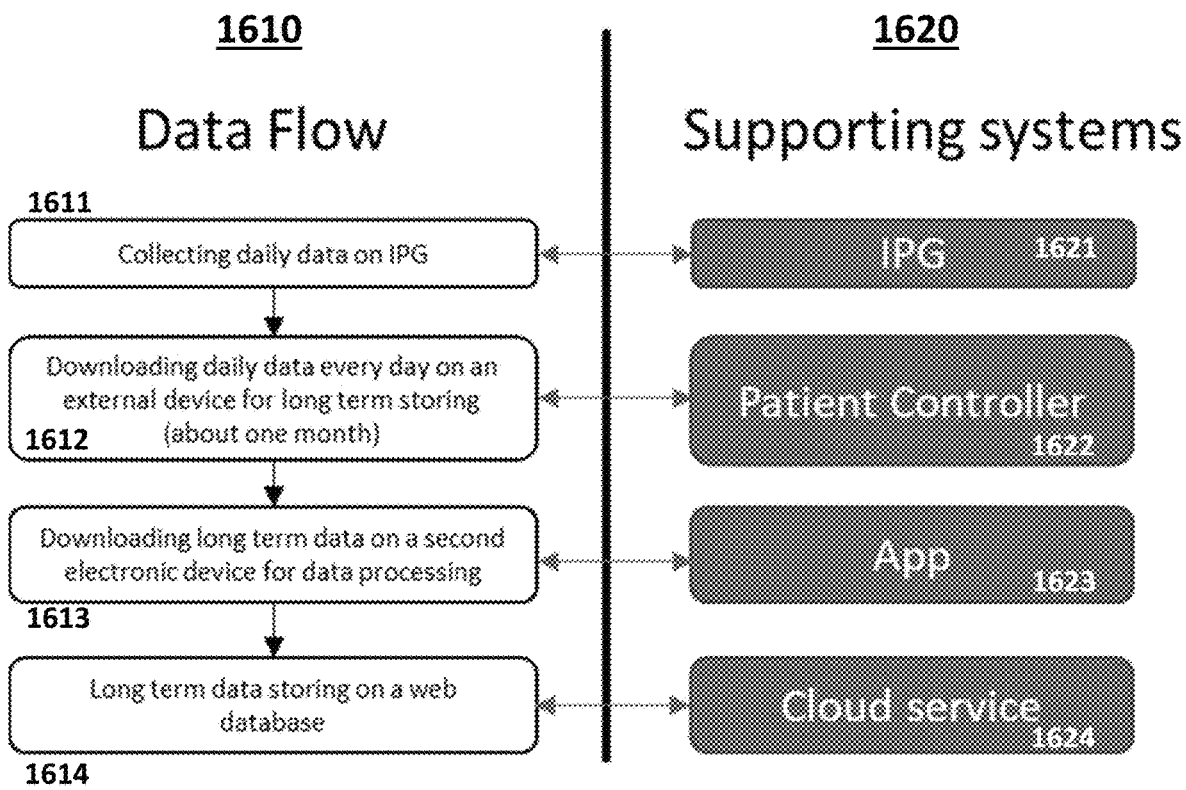
FIG. 16 is a flow chart of an exemplary communications method and data flow between supporting components of a deep brain stimulation system.

FIG. 16 is a flow chart of an exemplary communications method and data flow 1610 between supporting component (also referred to as 'supporting systems') 1620 of a deep brain stimulation system (such as the deep brain stimulation system 100 as shown and described with respect to FIG. 1), in some variations. The deep brain stimulation may implement the data flow 1610 using the supporting components 1620. The supporting components may include an IPG 1621 (implantable device 101 of FIG. 1), a patient controller 1622 (patient personal controller device 111 of FIG. 1), an application 1623 (implemented in the user compute device 121 of FIG. 1 or the clinician programmer device 131), a cloud service (biobank server of FIG. 1) 1624. The data flow includes collecting 1610 daily data on the IPG device. The daily data may include a set of neural activity signal records and/or patient log data. The data flow includes downloading 1612 daily data every day on the patient controller 1622 for a long-term data storage. The data flow includes downloading long term data on the application 1623. The data flow includes transmitting and storing 1614 the long term data to/in the cloud service 1624.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to explain the principles of the invention and its practical applications, they thereby enable others skilled in the art to utilize the invention and various variations with various modifications as are suited to the particular use contemplated. It is intended that the following claims and their equivalents define the scope of the invention.

What is claimed is:
1. A system comprising:
an implantable device configured to acquire and store neural activity signal records from a patient implanted with the implantable device and apply electrical stimulation to the patient;
a personal controller device configured to establish a first wireless connection with the implantable device, wherein the personal controller device is configured to transmit power to the implantable device and the implantable device is configured to transmit neural activity signal records to the personal controller device over the first wireless connection; and
a clinician programmer device configured to receive the neural activity signal records from the implantable device by establishing a second wireless connection based on activation of the first wireless connection,
wherein the clinician programmer device is configured to set a plurality of stimulation parameters for the patient based on the neural activity signal records, and
wherein the first wireless connection comprises an inductive link, the power is an inductive power induced from the personal controller device to the implantable device via the inductive link for recharging the implantable device, and the implantable device is configured to transmit at least one of the neural activity signal records to the personal controller during the recharging.

2. The system of claim 1, further including a user compute device configured to:
   receive patient log data;
   associate the patient log data and the neural activity signal records based on at least a time correlation between the patient log data and the neural activity signal records;
   determine a plurality of medication-on time intervals and a plurality of medication-off time intervals based on the neural activity signal records and the patient log data; and
   generate the plurality of stimulation parameters according to the neural activity signal records during the plurality of medication-on time intervals and the medication-off time intervals.

3. The system of claim 2, wherein the user compute device is further configured to:
   generate a statistical distribution of the neural activity signal records including a plurality of average values and a plurality of a variance values; and
   display, via a user interface, a plot of the neural activity signal records, the plurality of average values, and the plurality of a variance values.

4. The system of claim 2, wherein the user compute device is further configured to:
   extract a plurality of spectral features within a frequency band of the neural activity signal records that are recorded during a predefined time period;
   determine a plurality of medication-on time intervals and a plurality of medication-off time intervals during the predefined time period; and
   generate a first average value of the plurality of spectral features within the plurality of medication-on time intervals of the frequency band and a second average value of the plurality of spectral features within the plurality of medication-off time intervals of the frequency band.

5. The system of claim 4, wherein the user compute device is configured to generate the plurality of stimulation parameters based on the first average value and the second average value.

6. The system of claim 2, wherein the user compute device is further configured to:
   train a machine learning model based on a set of historical neural activity signal records not including the neural activity signal records, or a set of historical stimulation parameters not including the plurality of stimulation parameters; and
   execute the machine learning model based on the neural activity signal records to identify the plurality of stimulation parameters.

7. The system of claim 2, wherein the user compute device is further configured to:
   transmit at least one of the neural activity signal records, the patient log data, or the plurality of stimulation parameters to a biobank server, and
   delete at least one of the neural activity signal records, the patient log data, or the plurality of stimulation parameters from a memory of the user compute device.

8. The system of claim 1, wherein the clinician programmer device is configured to establish an authenticated communication channel with the personal controller device, the clinician programmer device is further configured to:
   receive patient log data from the personal controller device;
   associate the patient log data and the neural activity signal records based on at least a time correlation between the patient log data and the neural activity signal records;
   determine a plurality of medication-on time intervals and a plurality of medication-off time intervals based on the neural activity signal records and the patient log data; and
   generate the plurality of stimulation parameters according to the neural activity signal records during the plurality of medication-on time intervals and the medication-off time intervals.

9. The system of claim 8, wherein the clinician programmer device is further configured to:
   generate a statistical distribution of the neural activity signal records including a plurality of average values and a plurality of a variance values; and
   display, via a user interface, a plot of the neural activity signal records, the plurality of average values, and the plurality of a variance values.

10. The system of claim 8, wherein the clinician programmer device is further configured to:
    extract a plurality of spectral features within a frequency band of the neural activity signal records that are recorded during a predefined time period;
    determine a plurality of medication-on time intervals and a plurality of medication-off time intervals during the predefined time period; and
    generate a first average value of the plurality of spectral features within the plurality of medication-on time intervals of the frequency band and a second average value of the plurality of spectral features within the plurality of medication-off time intervals of the frequency band.

11. The system of claim 8, wherein the clinician programmer device is further configured to:
    transmit at least one of the neural activity signal records, the patient log data, or the plurality of stimulation parameters to a biobank server, and
    delete the at least one of the neural activity signal records, the patient log data, or the plurality of stimulation parameters from a memory of the clinician programmer device.

12. A system comprising:
    an implantable device configured to acquire and store neural activity signal records from a patient implanted with the implantable device and apply electrical stimulations to the patient;
    a personal controller device configured to establish a first wireless connection to the implantable device, wherein the personal controller device is configured to transmit power to the implantable device and the implantable device is configured to transmit neural activity signal records to the personal controller device over the first wireless connection; and
    a clinician programmer device configured to:
      establish a second wireless connection to the implantable device, the second wireless connection based on activation of the first wireless connection;
      receive, via the second wireless connection, the neural activity signal records from the implantable device; and
      generate a plurality of stimulation parameters according to the neural activity signal records, wherein the first wireless connection comprises an inductive link, the power is an inductive power induced from the personal controller device to the implantable device via the inductive link for recharging the implantable device, and the implantable device is configured to transmit at least one of the neural activity signal records to the personal controller device during the recharging.

13. The system of claim 12, further comprising a user compute device configured to establish a third wireless connection to the personal controller device, the user compute device is configured to:
   receive, via the third wireless connection, the neural activity signal records from the personal controller device,
   receive patient log data from the personal controller device, and
   determine a plurality of medication-on time intervals and a plurality of medication-off time intervals based on at least one of the neural activity signal records and the patient log data.

14. The system of claim 13, wherein at least one of the user compute device or the clinician programmer device is further configured to:
   transmit at least one of the neural activity signal records, the patient log data, the plurality of stimulation parameters to a biobank server either directly or through a user compute device, and
   delete the at least one of the neural activity signal records, the patient log data, or the plurality of stimulation parameters from the at least one of a memory of the user compute device or a memory of the clinician programmer device.

* * * * *